US009061038B2

(12) United States Patent
Garland et al.

(10) Patent No.: US 9,061,038 B2
(45) Date of Patent: *Jun. 23, 2015

(54) DOXORUBICIN ADJUVANTS TO REDUCE TOXICITY AND METHODS FOR USING THE SAME

(75) Inventors: William A. Garland, San Clemente, CA (US); Brian D. Frenzel, Los Altos, CA (US)

(73) Assignee: Tosk, Incorporated, Mountain View, CA (US)

( * ) Notice: Subject to any disclaimer, the term of this patent is extended or adjusted under 35 U.S.C. 154(b) by 389 days.

This patent is subject to a terminal disclaimer.

(21) Appl. No.: 13/532,519

(22) Filed: Jun. 25, 2012

(65) Prior Publication Data
US 2012/0329744 A1 Dec. 27, 2012

Related U.S. Application Data

(63) Continuation of application No. 12/369,657, filed on Feb. 11, 2009, now Pat. No. 8,227,517.

(60) Provisional application No. 61/028,090, filed on Feb. 12, 2008.

(51) Int. Cl.
C07C 321/22 (2006.01)
C07C 321/24 (2006.01)
C07C 321/26 (2006.01)
A61K 31/704 (2006.01)
A61K 31/15 (2006.01)
C07C 323/47 (2006.01)

(52) U.S. Cl.
CPC ............. *A61K 31/704* (2013.01); *C07C 321/26* (2013.01); *C07C 321/24* (2013.01); *C07C 321/22* (2013.01); *A61K 31/15* (2013.01); *C07C 323/47* (2013.01)

(58) Field of Classification Search
None
See application file for complete search history.

(56) References Cited

U.S. PATENT DOCUMENTS

| 5,025,032 | A | 6/1991 | Carney et al. |
|---|---|---|---|
| 5,036,097 | A | 7/1991 | Floyd et al. |
| 5,508,305 | A | 4/1996 | Carney et al. |
| 5,723,502 | A | 3/1998 | Proctor |
| 5,780,510 | A | 7/1998 | Carney |
| 6,002,001 | A | 12/1999 | Carney et al. |
| 6,083,988 | A | 7/2000 | Becker |
| 6,083,989 | A | 7/2000 | Flitter et al. |
| 6,107,315 | A | 8/2000 | Carney et al. |
| 6,197,825 | B1 | 3/2001 | Becker |
| 6,291,702 | B1 | 9/2001 | Becker |
| 6,342,523 | B1 | 1/2002 | Waterbury et al. |
| 6,403,627 | B1 | 6/2002 | Carney et al. |
| 6,479,697 | B2 | 11/2002 | Kruk et al. |
| 6,689,911 | B2 | 2/2004 | Kruk et al. |
| 6,730,700 | B2 | 5/2004 | Waterbury et al. |
| 6,998,419 | B2 | 2/2006 | Waterbury et al. |
| 2001/0056108 | A1 | 12/2001 | Lai |
| 2003/0108484 | A1 | 6/2003 | Leyland-Jones |
| 2005/0059638 | A1 | 3/2005 | Kelly et al. |
| 2005/0192281 | A1 | 9/2005 | Kelly et al. |

FOREIGN PATENT DOCUMENTS

| JP | H09-507232 A | 7/1997 |
|---|---|---|
| JP | 2007-509840 A | 4/2007 |
| WO | WO 92/22290 A1 | 12/1992 |
| WO | 9517876 | 7/1995 |
| WO | WO 2007/118947 A1 | 10/2007 |

OTHER PUBLICATIONS

West et al., "Contrast Enhancement Materials for MID-UV Applications" SPIE (1988) vol. 920 pp. 75-81.*
Braga et al., "Making Crystals from Crystals: a green route to crystal engineering and polymorphism" Chemical Communications (2005) pp. 3635-3645.
Cvetkovic et al., "Dexrazoxane: A Review of Its Use for Cardioprotection During Anthracycline Chemotherapy"; ADIS Drug Evaluation; Drugs (2005), 65 (7); 1005-1024.
Hasinoff, B et al., "Dexrazoxane use in the prevention of anthracycline extravasation injury"; Drug Evaluation; Future Oncol. (2006) 2(1), 15-20.
Hochster, H. "Clinical Pharmacology of Dexrazoxane"; Seminars in Oncology, vol. 25, No. 4, Suppl 10, Aug. 1998 pp. 37-42.
Jain et al., "Polymorphism in Pharmacy" Indian Drugs (1986) vol. 23 No. 6, pp. 315-329.
Jotti et al., "Cardiotoxicity Induced by Doxorubicin In Vivo: Protective Activity of the Spin Trap Alpha-Phenyl-Tert-Butyl Nitrone" Pharmacological Research (1992) vol. 26 No. 2 pp. 143-150.
Kotamaraju et al., "Doxorubicin-induced apoptosis inendothelial cells and a cardiomyocytes is ameliorated by nitrone spin traps and ebselen"; J. Biol. Chem. (2000); v275: pp. 33585-33592.
Lee J. H. et al., "Protective role of alpha-phenyl-N-t-butylinitrone against ionizing radiation in U937 cells and mice" Cancer Research vol. 63, No. 15 (2003) pp. 6885-6893.
Lee J. H. et al., "The effect of alpha-phynyl-N-t-buytlnitrone on ionizing raditation-induced apoptosis in U937 cells" Free Radical Research, vol. 39, No. 12 (2005) pp. 1325-1333.

(Continued)

Primary Examiner — Eric Olson
(74) Attorney, Agent, or Firm — Bret E. Field; Glenn J. Foulds; Bozicevic, Field & Francis LLP

(57) ABSTRACT

Methods are provided for using doxorubicin active agents in which reduced host toxicity is observed. Aspects of the methods including administering to a subject an effective amount of a doxorubicin active agent in conjunction with a doxorubicin toxicity-reducing adjuvant, e.g., a nitrone compound, or a nitrone compound in combination with a bisdioxopiperazine compound. Also provided are compositions for use in practicing the subject methods. The methods and compositions find use in a variety of different applications, including in the treatment of a variety of different disease conditions.

19 Claims, 3 Drawing Sheets

(56) References Cited

OTHER PUBLICATIONS

Lieberman et al., "Pharmaceutical Dosage Forms" vol. 2, published 1990 by Marcel Dekker, Inc, pp. 462-472.

Marty et al., "Multicenter randomized phase III study of the caridoprotective effect of dexrazoxane (Cardioxane) in advancved/metastatic breast cancer patients treated with anthracycline-based chemotherapy"; Annals of Oncology 17:614-622 (2006).

The Merck Manual of Diagnosis and Therapy, Seventeenth Edition, published 1999 by Merck Research Laboratories, pp. 973-995.

Seymour et al., "Use of dexrazoxane as a cardioprotectant in patients receiving doxorubicin or epirubicin chemotherapy for the treatment of cancer"; Cancer Prevention & Control, (1999) 3(2) pp. 145-159.

Silverman, The Organic Chemistry of Drug Design and Drug Action, published 1992 by Merck Research Laboratories, pp. 352-397.

Vippagunta et al., "Crystalline Solids" Advanced Drug Delivery Reviews (2001) vol. 48 pp. 3-26.

Yijima et al., "13C and 1H NMR of alpha-arylnitrones. Subsequent Effects on the alpha-position of alpha-(p-Substituted Phenyl)nitrones" Bulletin of the Chemical Society of Japan (1986) vol. 59 pp. 2165-2170.

Ortial et al., "Fluorinated Amphiphilic Amino Acid Derivatives as Antioxidant Carriers: A New Class of Protective Agents", Journal of Medicinal Chemistry, vol. 49, No. 9, pp. 2812-2820 (2006).

* cited by examiner

DOXORUBICIN ADJUVANTS TO REDUCE TOXICITY AND METHODS FOR USING THE SAME

CROSS REFERENCE TO RELATED APPLICATIONS

Pursuant to 35 U.S.C. §119 (e), this application claims priority to the filing date of the U.S. Provisional Patent Application Ser. No. 61/028,090 filed Feb. 12, 2009; the disclosure of which is herein incorporated by reference.

INTRODUCTION

Doxorubicin or hydroxyldaunorubicin is an antineoplastic drug widely used in chemotherapy (Hortobágyi, Drugs, 54 (Supplement 4):1-7 (1997)). It is an anthracycline antibiotic and structurally closely related to daunomycin (Minotti et al., Pharmacologiy. Rev., 56; 185-229 (2004). Doxorubicin (DOX) is commonly used in the treatment of a wide range of cancers, including cancers of the blood, lymph system, bladder, breast, stomach, lung, ovaries, thyroid, nerves, kidneys, bones, soft tissues, including muscles and tendons, multiple myeloma, and others.

Doxorubicin is a highly toxic drug. Cardiotoxicity is its most important, dose limiting toxicity (Outomuro et al., Int J. Cardiol., 117: 6-15 (2007)). As the cumulative dose of doxorubicin increases, the risk of developing cardiac side effects, including congestive heart failure, dilated cardiomyopathy and death, increases as well.

Attempts to minimize the toxicity of doxorubicin have included combination chemotherapy, synthesis of doxorubicin analogues, antibody conjugates, immunotherapy and entrapment in liposomes. One combination employs dexrazoxane (4-[1-(3,5-dioxopiperazin-1-yl) propan-2-yl]piperazine-2,6-dione), which is a cardioprotectant agent used to reduce the risk of cardiotoxicity (Hellmann, Semin Oncol, 25: 48-54 (1998) and Hasinoff and Herman Cardioiovasc Toxicol, 7:140-144 (2007). Liposomel formulations combining daunorubicin and doxorubicin also appear to yield reduced cardiotoxicity (Batist, Cardiovasc Toxicol, 7: 72-4 (2007). However, the problem has not been solved, and there is continued interest in finding new ways to reduce doxorubicin toxicity.

Nitrones are the N-oxide of imines first used as agents to trap free-radicals (known as spin trapping) in chemical systems and, subsequently, in biochemical systems. Nitrones have been found to have potential in the treatment of neurodegenerative diseases and other aging-related diseases, such as stroke, Alzheimer's disease and the development of cancer. (Floyd et al., Free Radical Biology and Medicine, 45, 1361-1374 (2008)). Besides decreasing oxidative stress and limiting oxidative damage, nitrones have also demonstrate anti-inflammatory activity in animal models of inflammation-associated diseases by altering cellular signaling processes (Floyd et al., Free Radical Biology and Medicine, 45, 1361-1374 (2008)).

α-phenyl-N-tert-butyl nitrone ("PBN") is a widely researched nitrone which has been found to have potent pharmacologic activities in various neurodegenerative and aging-related disease models (Maples et al., CNS Drugs, 18(15), 1071-1084 (2004); Green et al., Pharmacol. Ther., 100(3), 195-214 (2003); Floyd et al., Ann. N.Y. Acad. Sci., 959, 321-329 (2002); Floyd et al., Mech. Ageing Dev., 123(8), 1021-1031 (2002); Kotake, Antioxid. Redox Signal., 1(4), 481-499 (1999)).

SUMMARY

Methods of using doxorubicin active agents in which reduced host toxicity is observed are provided. In the subject methods, an effective amount of a doxorubicin active agent is administered to the host in conjunction with the administration of a doxorubicin toxicity-reducing adjuvant of the present invention, where the doxorubicin active agent and doxorubicin toxicity-reducing adjuvant may be administered sequentially, simultaneously, or any combination thereof. The doxorubicin toxicity-reducing adjuvant is a compound containing a nitrone functionality. Also provided are compositions for use in practicing the subject methods, e.g., doxorubicin pharmaceutical compositions having reduced toxicity and kits that include the same. Compositions comprising thiol-modified nitrones also are provided that find use in the subject methods as well as other applications typical of, or which benefit by the use of, nitrone compounds in general. Thus, the subject methods and compositions find use in a variety of different applications, including the treatment of a variety of different disease conditions. An exemplary application illustrating a significant advantage of the methods and compositions of the invention is the reduction of doxorubicin-induced cardiac damage.

DEFINITIONS

Figure 1:
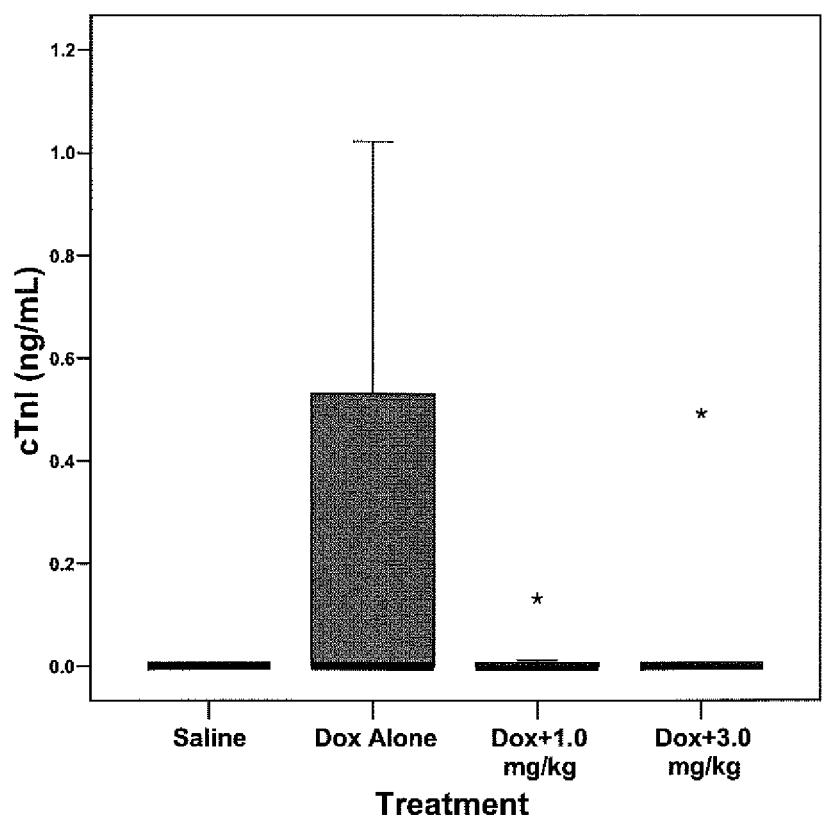
FIG. 1 depicts a set of data demonstrating the ability of TK-115339, a representative nitrone test article, to mitigate one aspect of doxorubicin-induced toxicity, cardiac damage in CD-1 mice as determined by concentration of cardiac troponin I (cTnI) in animal plasma.

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. By way of non-limiting example, such substituents may include e.g. halo (such as fluoro, chloro, bromo), —CN, —CF$_3$, —OH, —OCF$_3$, C$_{2-6}$ alkenyl, C$_{3-6}$ alkynyl, C$_{1-6}$ alkoxy, aryl and di-Cl_6 alkylamino.

"Acyl" refers to a radical —C(O)R, where R is hydrogen, alkyl, cycloalkyl, cycloheteroalkyl, aryl, arylalkyl, heteroalkyl, heteroaryl or heteroarylalkyl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, cycloheteroalkyl, aryl, arylalkyl, heteroalkyl, heteroaryl, heteroarylalkyl and R is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzyl-carbonylamino and the like.

"Acyloxy" refers to the group —OC(O)H, —OC(O)-alkyl, —OC(O)-aryl or —OC(O)-cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to 6 or 12 carbon atoms.

"Alkanoyl" or "acyl" as used herein refers to the group —C(O)H or —C(O)-alkyl.

"Alkenyl" refers to monovalent olefinically unsaturated hydrocarbyl groups having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkoxy" refers to the group —O-alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxyamino" refers to a radical —N(H)O-alkyl or —N(H)O-cycloalkyl as defined herein.

"Alkoxycarbonyl" refers to a radical —C(O)-alkoxy where alkoxy is as defined herein.

"Alkoxycarbonylamino" refers to the group —NRC(O)OR' where R is hydrogen, alkyl, aryl or cycloalkyl, and R' is alkyl or cycloalkyl.

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Alkylamino" refers to a radical alkyl-NRR', wherein each of R and R' are independently selected from hydrogen and alkyl.

"Alkylarylamino" refers to a radical —NRR' where R represents an alkyl or cycloalkyl group and R' is an aryl as defined herein.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkylthio" refers to a radical —S-alkyl or —S-cycloalkyl group as defined herein that may be optionally substituted as defined herein. Representative examples include, but are not limited to, methylthio, ethylthio, propylthio, butylthio, and the like.

"Alkynyl" refers to acetylenically unsaturated hydrocarbyl groups particularly having up to about 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Amino" refers to the radical —NH$_2$.

"Aminocarbonyl" refers to the group —C(O)NRR where each R is independently hydrogen, alkyl, aryl or cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalkyl, or where the R groups are joined to form an alkylene group.

"Aminohydroxyphosphoryl" refers to the radical —PO(OH)NH$_2$.

"Aralkyl" or "arylalkyl" refers to an alkyl group, as defined above, substituted with one or more aryl groups, as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Arylalkyloxy" refers to an —O-arylalkyl radical where arylalkyl is as defined herein.

"Arylamino" refers to the group aryl-NRR', wherein each of R and R' are independently selected from hydrogen, aryl and heteroaryl.

"Aryloxy" refers to —O-aryl groups wherein "aryl" is as defined herein.

"Arylsulfonyl" refers to a radical —S(O)$_2$R where R is an aryl or heteroaryl group as defined herein.

"Azido" refers to the radical —N$_3$.

"Carbamoyl" refers to the radical —C(O)N(R)$_2$ where each R group is independently hydrogen, alkyl, cycloalkyl or aryl, as defined herein, which may be optionally substituted as defined herein.

"Carboxy" refers to the radical —C(O)OH.

"Cyano" refers to the radical —CN.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

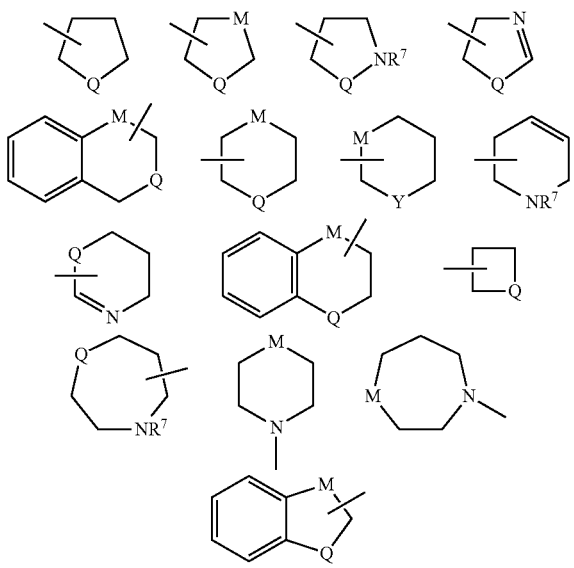

optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives. In the examples, M is $CR^7$, $NR^3$, O, or S; Q is O, $NR^3$ or S.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Dihydroxyphosphoryl" refers to the radical —PO(OH)$_2$.

"Doxorubicin pharmaceutical composition" refers to a doxorubicin active agent used in combination with a doxorubicin toxicity-reducing adjuvant, either to be administered separately on in a combined formulation.

"Halo" or "halogen" refers to fluoro, chloro, bromo and iodo. Halo groups can be either fluoro or chloro.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms. Examples of representative cycloheteroalkenyls include the following:

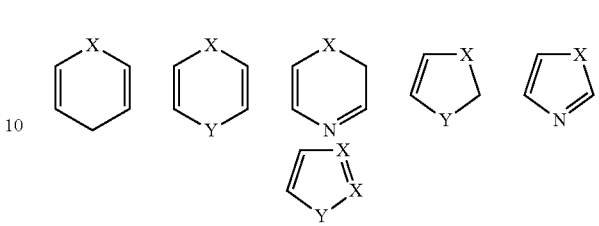

wherein each X is selected from $CR^5$, $NR^5$, O and S; and each Y is selected from carbonyl, N, $NR^5$, O and S.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is a 5-20 membered heteroaryl, or 5-10 membered heteroaryl. Particular heteroaryl groups are those derived from thiophen, pyrrole, benzothiophene, benzofuran, indole, pyridine, quinoline, imidazole, oxazole and pyrazine. Examples of representative heteroaryls include the following:

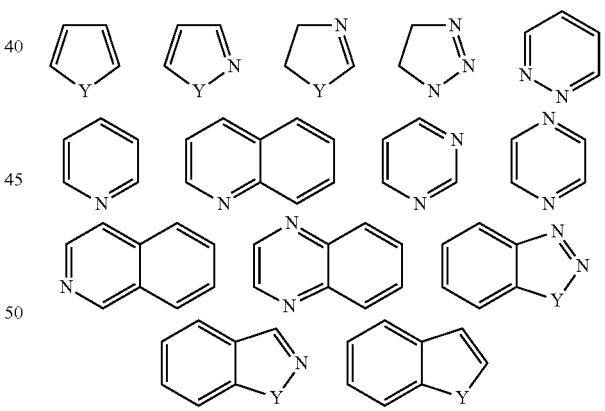

wherein each Y is selected from carbonyl, N, $NR^5$, O, and S. Examples of representative aryl having hetero atoms containing substitution include the following:

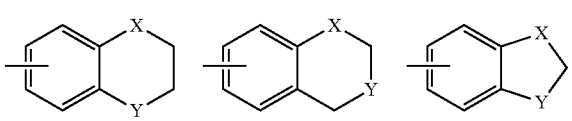

wherein each X is selected from C—$R^5$, $C(R^5)_2$, $NR^5$, O and S; and each Y is selected from carbonyl, $NR^5$, O and S.

"Hydroxyl" refers to the radical —OH.

"Nitro" refers to the radical —NO$_2$.

"$R^1$" is each independently selected from the group consisting of substituted or unsubstituted aliphatic, substituted or unsubstituted alkyl, substituted or unsubstituted heteroalkyl, substituted or unsubstituted aryl, substituted or unsubstituted heteroaryl, substituted or unsubstituted aralkyl, and substituted or unsubstituted heteroaralkyl.

"$R^2$" and "$R^3$" are each independently selected from the group consisting of hydrogen, substituted or unsubstituted alkyl, substituted or unsubstituted cycloalkyl, substituted or unsubstituted aryl, substituted or unsubstituted heteroaryl, and substituted or unsubstituted aralkyl.

"$R^4$" is each independently selected from the group consisting of hydrogen, substituted or unsubstituted alkyl, substituted or unsubstituted cycloalkyl, substituted or unsubstituted aryl, and substituted or unsubstituted aralkyl, and any two $R^4$s may join together to form a cycloalkyl, cycloheteroalkyl ring.

"$R^5$" is each independently hydrogen, alkyl, substituted alkyl, acyl, substituted acyl, acylamino, substituted acylamino, alkylamino, substituted alkylamino, alkylthio, substituted alkylthio, alkoxy, substituted alkoxy, alkoxycarbonyl, substituted alkoxycarbonyl, alkylarylamino, substituted alkylarylamino, arylalkyloxy, substituted arylalkyloxy, amino, aryl, substituted aryl, arylalkyl, substituted arylalkyl, sulfoxide, substituted sulfoxide, sulfone, substituted sulfone, sulfanyl, substituted sulfanyl, aminosulfonyl, substituted aminosulfonyl, arylsulfonyl, substituted arylsulfonyl, sulfonic acid, sulfonic acid ester (i.e., sulfonate), dihydroxyphosphoryl, substituted dihydroxyphosphoryl, aminohydroxyphosphoryl, substituted aminohydroxyphosphoryl, azido, carboxy, substituted carboxy (i.e., ester), carbamoyl, substituted carbamoyl, cyano, cycloalkyl, substituted cycloalkyl, cycloheteroalkyl, substituted cycloheteroalkyl, dialkylamino, substituted dialkylamino, halo, heteroaryloxy, substituted heteroaryloxy, heteroaryl, substituted heteroaryl, heteroalkyl, substituted heteroalkyl, hydroxyl, nitro or thio.

"$R^6$" is selected from the group consisting of hydrogen, —SR$^7$, —SO$_2$R$^7$, SO$_2$NR$^7$R$^8$, —SO$_3$R$^7$, —CONR$^7$R$^8$, —NR$^7$R$^8$, —OH, —PO(OR$^7$)NR$^8$R$^9$, —PO(OR$^7$)$_2$ and —CO$_2$R$^7$.

"$R^7$", "$R^8$", and "$R^9$" are independently selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"$R^{10}$", "$R^{11}$", and "$R^{12}$" are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"$R^{13}$" and "$R^{20}$" are independently hydrogen, alkyl, alkenyl, alkynyl, cycloheteroalkyl, alkanoyl, alkoxy, aryloxy, heteroaryloxy, alkylamino, arylamino, heteroarylamino, NR$^{10}$COR$^{11}$, NR$^{10}$SOR$^{11}$, NR$^{10}$SO$_2$R$^{14}$, COOalkyl, COOaryl, CONR$^{10}$R$^{11}$, CONR$^{10}$OR$^{11}$, NR$^{10}$R$^{11}$, SO$_2$NR$^{10}$R$^{11}$, S-alkyl, S-alkyl, SOalkyl, SO$_2$alkyl, Saryl, SOaryl, or SO$_2$aryl; or $R^{13}$ and $R^{20}$ form a cyclic ring (saturated or unsaturated) from 5 to 8 atoms, optionally containing one or more heteroatoms selected from the group N, O or S.

"$R^{14}$", "$R^{15}$", "$R^{16}$", and "$R^{17}$" are independently hydrogen, alkyl, substituted alkyl, aryl, arylalkyl, cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{18}$R$^{19}$, —C(O)R$^{18}$ or —S(O)$_2$R$^{18}$ or optionally R$^{18}$ and R$^{19}$ together with the atom to which they are both attached form a cycloheteroalkyl or substituted cycloheteroalkyl ring.

"$R^{18}$", "$R^{19}$", and "$R^{22}$" are each independently selected from the group consisting of hydrogen, substituted or unsubstituted alkyl, substituted or unsubstituted aryl, substituted or unsubstituted arylalkyl, substituted or unsubstituted cycloalkyl, substituted or unsubstituted cycloheteroalkyl, substituted or unsubstituted heteroalkyl, substituted or unsubstituted heteroaryl, and substituted or unsubstituted heteroarylalkyl.

"$R^{21}$" is $R^{22}$ or —S—R$^{22}$.

"Spatial isomers" refers to isomers other than structural isomers. Examples include, but are not limited to, stereoisomers such as enantiomers, diastereomers, geometric isomers, tautomers, cis-trans isomers, isotopic isomers, and spin isomers.

"Substituted" refers to a group in which one or more hydrogen atoms are each independently replaced with the same or different substituent(s). Typical substituents include, but are not limited to, —X, —R$^{14}$, —O—, =O, —OR$^{14}$, —SR$^{14}$, —S$^-$, =S, —NR$^{14}$R$^{15}$, =NR$^{14}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{14}$, —OS(O$_2$)O$^-$, —OS(O)$_2$R$^{14}$, —P(O)(O—)$_2$, —P(O)(OR$^{14}$)(O$^-$), —OP(O)(OR$^{14}$)(OR$^{15}$), —C(O)R$^{14}$, —C(S)R$^{14}$, —C(O)OR$^{14}$, —C(O)NR$^{14}$R$^{15}$, —C(O)O$^-$, —C(S)OR$^{14}$, —NR$^{16}$C(O)NR$^{14}$R$^{15}$, —NR$^{16}$C(S)NR$^{14}$R$^{15}$, —NR$^{17}$C(NR$^{16}$)NR$^{14}$R$^{15}$ and —C(NR$^{16}$)NR$^{14}$R$^{15}$, where each X is independently a halogen.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylannino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group.

"Substituted aminohydroxyphosphoryl" includes those groups recited in the definition of "substituted" herein, and particularly refers to an aminohydroxyphosphoryl wherein the amino group is substituted with one or two substituents. In certain embodiments, the hydroxyl group can also be substituted.

"Substituted aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—. Examples of representative substituted aryls include the following structures:

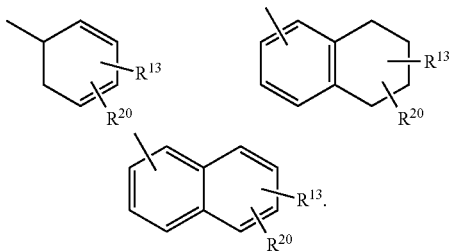

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Substituted dihydroxyphosphoryl" includes those groups recited in the definition of "substituted" herein, and particularly refers to a dihydroxyphosphoryl radical wherein one or both of the hydroxyl groups are substituted.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$.

"Sulfanyl" refers to the radical —SH. "Substituted sulfanyl" refers to a radical such as —SR wherein R is any substituent described herein.

"Sulfone" refers to the group —SO$_2$R. In particular embodiments, R is selected from H, lower alkyl, alkyl, aryl and heteroaryl.

"Sulfonyl" refers to the divalent radical —S(O$_2$)—. "Substituted sulfonyl" refers to a radical such as R—(O$_2$)S— wherein R is any substituent described herein. "Aminosulfonyl" refers to the radical H$_2$N(O$_2$)S—, and "substituted aminosulfonyl" refers to a radical such as R$_2$N(O$_2$)S— wherein each R is independently any substituent described herein.

"Thioalkoxy" refers to the group —S-alkyl.
"Thioaryloxy" refers to the group —S-aryl.
"Thioketo" refers to the group =S.
"Thiol" refers to the group —SH.

One having ordinary skill in the art will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

DETAILED DESCRIPTION

Methods are provided for using doxorubicin active agents in which reduced host toxicity is observed. In the subject methods, an effective amount of a doxorubicin active agent is administered to the host in conjunction with the administration of a doxorubicin toxicity-reducing adjuvant of the present invention, where the doxorubicin active agent and doxorubicin toxicity-reducing adjuvant may be administered sequentially, simultaneously, or any combination thereof. Also provided are compositions for use in practicing the subject methods, e.g., doxorubicin pharmaceutical compositions having reduced toxicity and kits that include the same. Compositions comprising thiol-modified nitrones also are provided that find use in the subject methods as well as other applications typical of, or which benefit by the use of, nitrone compounds in general. The subject methods and compositions find use in a variety of different applications, including the treatment of a variety of different disease conditions. An exemplary application illustrating a significant advantage of the methods and compositions of the invention is the reduction of doxorubicin-induced cardiac damage Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the subject invention, the subject methods are described first in greater detail, followed by a review of the various compositions, e.g., formulations and kits, that may find use in the subject methods, as well as a discussion of various representative applications in which the subject methods and compositions find use.

Methods

As summarized above, the subject invention provides methods of administering a doxorubicin active agent to a subject in need thereof, e.g., for the treatment of a host suffering from disease or condition treatable by a doxorubicin active agent (as described in greater detail below). An aspect of the subject methods is that the doxorubicin active agent is administered to the subject in combination with a doxorubicin toxicity-reducing adjuvant which is a nitrone compound. By "in combination with" is meant that an amount of the doxorubicin toxicity-reducing adjuvant is administered anywhere from simultaneously to up to 5 hours or more, e.g., 10 hours, 15 hours, 20 hours or more, prior to or after the doxorubicin active agent. In certain embodiments, the doxorubicin active agent and doxorubicin toxicity-reducing adjuvant are administered sequentially, e.g., where the doxorubicin active agent is administered before or after the doxorubicin toxicity-reducing adjuvant. In yet other embodiments, the doxorubicin active agent and doxorubicin toxicity-reducing adjuvant are administered simultaneously, e.g., where the doxorubicin active agent and doxorubicin toxicity-reducing adjuvant are administered at the same time as two separate formulations or are combined into a single composition that is administered to the subject. Regardless of whether the doxorubicin active agent and doxorubicin toxicity-reducing adjuvant are administered sequentially or simultaneously, as illustrated above, the agents are considered to be administered together or in combination for purposes of the present invention. Routes of administration of the two agents may vary, where representative routes of administration are described in greater detail below.

In the subject methods, an effective amount of a doxorubicin active agent is administered to a host in need thereof in combination with an effective amount of a doxorubicin toxicity-reducing adjuvant. By doxorubicin active agent is meant doxorubicin or an analogue/derivative thereof, e.g., native doxorubicin and its analogues. Doxorubicin is an anthracycline antibiotic first isolated from the fungus *Streptomyces peucetius*. The chemical structure of doxorubicin consists of a tetracyclic ring, with the sugar daunosamine attached by a glycosidic linkage. Structurally, doxorubicin is related to daunomycin (daunorubicin) and differs only in hydroxyl group substitution (instead of hydrogen) at the alkyl side chain, at position '9' of the 'A' ring. However, daunorubicin is only useful for acute leukemia whereas doxorubicin can be used for a wide range of cancers. (See, "doxorubicin" content at www.fda.gov, in the 2007 Physicians Desk Reference and in other similar references). The hydrochloride salt of doxorubicin is one of the most common forms. It is referred to by various names, such as doxorubicin hydrochloride; 14-hydroxydaunorubicin hydrochloride; 3-hydroxyacetyldaunorubicin hydrochloride; and 5,12-naphthacenedione,10-[(3-amino-2,3,6-trideoxy-.alpha.-L-Iyxo-hexopyranosyl)oxy]-7,8,9,10-tetrahydro-6,8,11-trihydroxy-8-(hydroxyacetyl)-1-methoxy-, hydrochloride, (8S-cis)-(9CI). Doxorubicin hydrochloride has the molecular formula $C_{27}H_{29}NO_{11}$.HCl, a molecular weight (MW) of 580.0, and CAS number 25316-40-9. It is soluble in water and slightly soluble in methanol.

Doxorubicin can be thought of as a prototype compound for the anthracyclines daunorubicin, epirubicin and idarubicin. Although many derivatives of doxorubicin have been made in an attempt to reproduce the same or improved anti-tumor effects with less cardiac toxicity, doxorubicin remains the most widely administered of the anthracyclines. Nevertheless, a wide spectrum of analogues have been synthesized, offering a different antitumor spectrum, better therapeutic index and reduced toxicity than that offered by native doxorubicin (See, e.g., Weiss, R B, Semin Oncol., 19:670 (1992)). For example, analogues of doxorubicin have been made with similar to as much as 1000 times the anti-proliferative activity of the native compound, some with significantly reduced toxicity, and others with both attributes of anti-proliferative activity and reduced toxicity (Nagy et al., Proc Natl Acad Sci USA. 93 (6):2464 (1996); Nagy et al., Proc Natl Acad Sci USA. 95 (4):1794 (1998); Wasowska et al., Anticancer Res. 25(3B):2043 (2005); Fan et al., J Org. Chem. 72(8):2917 (2007); Zhang et al., J Med. Chem. 49(5):1792 (2006); Battisti et al., Mol. Pharm. 4(1):140 (2007); Fang et al., J Med. Chem. 49(3):932 (2006); Partugal at al., J Med. Chem. 48(26):8209 (2005); Haj et al., Chem Biol Interact. 145(3): 349 (2003); Suarato at al., Curr Pharm Des. 5(3):217 (1999); Chaires et al., J Med. Chem. 40(3):261 (1997); and Ripamonti et al., Invest New Drugs. 14(2):139 (1996)). While more toxic analogues are not desirable for intravenous administration in free form, such analogues may have use in Liposome-entrapped forms, which reduces drug toxicity.

Doxorubicin active agents of the present invention include doxorubicin and any analogues or derivatives thereof whose toxicity is reduced when administered in conjunction with a toxicity-reducing adjuvant according to the subject invention. Whether or not a given doxorubicin active agent is suitable for use according to the present invention can be readily determined using assays employed in the experimental section, below. Generally, a doxorubicin active agent is suitable for use in the subject methods if its toxicity is reduced by 2-fold or more, such as by 10-fold or more and including by 100-fold or more, which can be determined in vitro and/or in vivo as described in the Experimental section, below. In certain embodiments, the doxorubicin active agent is one that reduces the occurrence and/or intensity of observable toxic side effects as observed in the mouse assay described in the Experimental section below.

By doxorubicin toxicity-reducing adjuvant it is meant an agent that reduces unwanted toxicity of a doxorubicin active agent. Toxicity-reducing adjuvants of interest are those agents that reduce the toxicity of a doxorubicin active agent by 2-fold or more, such as by 10-fold and including by 100-fold or more, which can be determined in vitro and/or in vivo as described in the Experimental section, below. In certain embodiments, the toxicity-reducing adjuvants of interest are those that reduce the occurrence and/or intensity of observable toxic side effects of a given doxorubicin active agent, as observed in the mouse assay described in the Experimental section below.

The doxorubicin toxicity-reducing adjuvants of interest include nitrone compounds. In some embodiments, the nitrone is a compound of formula (I):

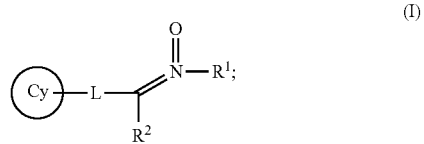

or a nitrone compound of formula (I) according to formula (II):

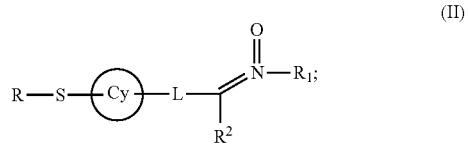

or a nitrone compound of formula (II) according to formula (III):

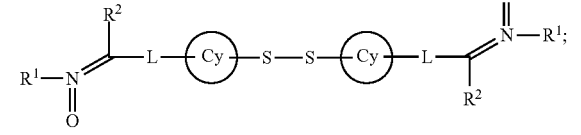

or the pharmaceutically acceptable salts, solvates, hydrates, and prodrug forms thereof, and spatial isomers thereof;

wherein:

L is —[C(R$^3$)$_2$]$_m$—X*—[C(R$^4$)$_2$]$_n$—; m is an integer from 0 to 6; n is an integer from 0 to 6;

X* is selected from the group consisting of no atom, NR$^3$, O, S, SO and SO$_2$;

R is hydrogen, thiol, or a thiol conjugate;

each Cy is independently selected from the group consisting of substituted or unsubstituted cycloalkyl, substituted or unsubstituted aryl, substituted or unsubstituted heteroaryl, substituted or unsubstituted cycloheteroalkyl, bicycloalkenyl, bicycloheteroalkenyl, bicycloaryl, or bicycloheteroaryl ring;

each R$^1$ is independently selected from the group consisting of substituted or unsubstituted aliphatic, substituted or unsubstituted alkyl, substituted or unsubstituted heteroalkyl, substituted or unsubstituted aryl, substituted or unsubstituted heteroaryl, substituted or unsubstituted aralkyl, and substituted or unsubstituted heteroaralkyl;

each R$^2$ is independently selected from the group consisting of hydrogen, substituted or unsubstituted alkyl, substituted or unsubstituted cycloalkyl, substituted or unsubstituted aryl, substituted or unsubstituted heteroaryl, and substituted or unsubstituted aralkyl;

each R$^3$ is independently selected from the group consisting of hydrogen, substituted or unsubstituted alkyl, substituted or unsubstituted cycloalkyl, substituted or unsubstituted aryl, substituted or unsubstituted heteroaryl, and substituted or unsubstituted aralkyl;

each R⁴ is independently selected from the group consisting of hydrogen, substituted or unsubstituted alkyl, substituted or unsubstituted cycloalkyl, substituted or unsubstituted aryl, and substituted or unsubstituted aralkyl, and any two R⁴s may join together to form a cycloalkyl, cycloheteroalkyl ring;

and one of Rᵃs and one of R⁴s on carbon atoms adjacent to X* may join together to form a heterocyclic ring of 5-7 atoms.

While the nitrone compounds in formulas (I), (II) and (III) depict one isomer of the carbon-nitrogen double bond of the nitrone functionalities, the scope of the present invention includes all geometric isomers of the nitrone compounds of formulas (I), (II) and (II) including, for example, all isomers (e.g., E and Z isomers) of the carbon-nitrogen double bond of each nitrone functionality. Each structure shown encompasses or represents both, or any one of, the E and Z isomers, or a mixture thereof.

With respect to the above formulas, it is noted that structures (I), (II) and (III) may also be written where the nitrone moiety does not include a double bond between the O and N, such that N carries a positive charge and O carries a negative charge. For example, structure II may be written as structure II(a):

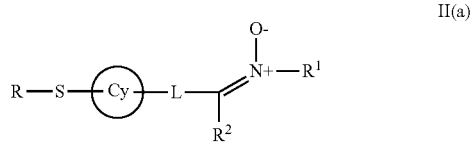

II(a)

Alternatively, the nitrone moiety be represented by a structure in which an arrow points from the N to the O, as shown in certain structures below.

In certain embodiments, the present invention provides aryl, heteroaromatic and bicyclic aryl nitrone compounds according to formulas (I), (II) or (III), and wherein Cy is

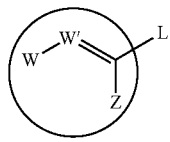

and wherein;

for aryl nitrones, W and Z are joined to form a substituted or unsubstituted cycloalkenyl or aryl ring of 5 to 8 atoms; for heteroaromatic nitrones, W and Z are joined to form a substituted or unsubstituted cycloheteroalkenyl or heteroaryl ring of 5 to 8 atoms; and for bicyclic aryl nitrones, W and Z are joined to form a bicycloalkenyl, bicycloheteroalkenyl, bicycloaryl, or bicycloheteroaryl ring of 8 to 11 atoms.

In certain embodiments, the present invention provides aryl and heteroaromatic nitrone compounds according to (I), (II) and (III) and wherein Cy is

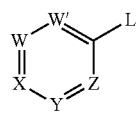

wherein: m' of W, W', X, Y and Z is N and the remainder are each independently C—R⁵; and m' is an integer from 0 to 3.

In certain embodiments, the present invention provides heteroaromatic nitrone compounds according to formulas (I), (II) or (III) and wherein Cy is

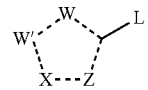

wherein: W, W', X, and Z is independently selected from C—R⁵, O, S, SO, SO₂, NR³ and N; and the dotted bond is single or double bond.

In certain embodiments, the present invention provides bicyclic aryl nitrone compounds according to formulas (I), (II) or (III) and wherein Cy is

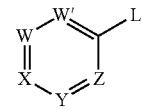

wherein W, W', X, Y and Z are members of a cycloalkenyl, aryl, cycloheteroalkenyl or heteroaryl ring; and any adjacent pair of W, W', X, Y and Z are further joined to form, together with the cycloalkenyl, aryl, cycloheteroalkenyl or heteroaryl ring comprising W, W', X, Y and Z, the bicycloalkenyl, bicycloheteroalkenyl, bicycloaryl, or bicycloheteroaryl ring.

In certain embodiments, the present invention provides bicyclic aryl nitrone compounds according to formulas (I), (II) or (III) and wherein Cy is selected from substituted or unsubstituted:

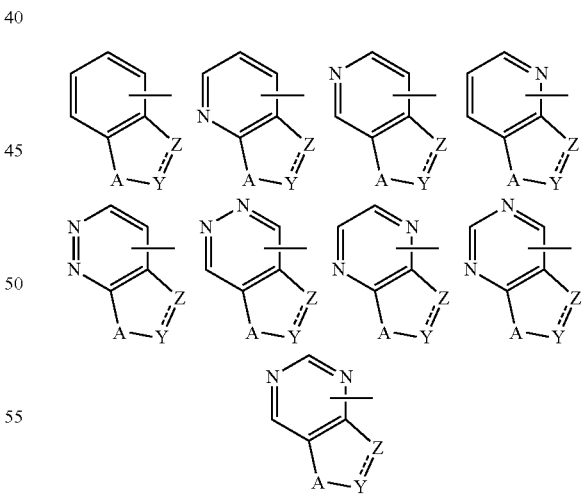

and wherein A, Y and Z are independently selected from C=O, CR⁵, NR³, O, and S; and the dotted line represents single or double bond.

In certain embodiments, the present invention provides bicyclic aryl nitrone compounds according to formulas (I), (II) or (III) and wherein Cy is selected from substituted or unsubstituted:

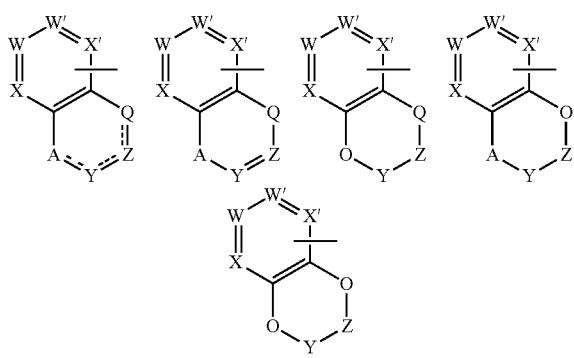

wherein W, W', X and X' are each independently $NR^3$ or $C-R^5$; Y and Z are each independently $C-R^5$ or carbonyl; A and Q are independently selected from $C-R^5$, $NR^3$, O, and S; and the dotted line represents single or double bond.

In certain embodiments, the present invention provides bicyclic aryl nitrone compounds according to formulas (I), (II) or (III) and wherein Cy is selected from substituted or unsubstituted:

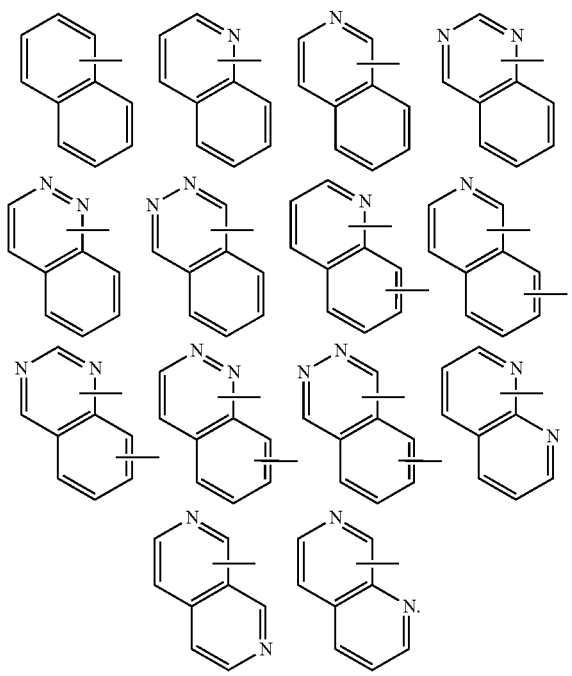

In certain embodiments, the present invention provides nitrone compounds according to formulas (I), (II) or (III) and wherein $R^2$ is hydrogen.

In certain embodiments, the present invention provides nitrone compounds according to formulas (I), (II) or (III) and wherein L is $-[C(R^3)_2]_m-X^*-[C(R^4)_2]_n-$.

In further embodiments, the present invention provides nitrone compounds according to formulas (I), (II) or (III) and wherein L is $-CH_2-X^*-[CH_2]_n-$.

In further embodiments, the present invention provides nitrone compounds according to formulas (I), (II) or (III) and wherein L is selected from $-CH_2-$, $-(CH_2)_2-$, $-(CH_2)_3-$, $-(CH_2)_4-$, $-(CH_2)_5-$, $-OCH_2-$, $-O(CH_2)_2-$, $-O(CH_2)_3-$, $-O(CH_2)_4-$, $-O(CH_2)_5-$, $-SCH_2-$, $-S(CH_2)_2-$, $-S(CH_2)_3-$, $-S(CH_2)_4-$, $-S(CH_2)_5-$, $-SOCH_2-$, $-SO(CH_2)_2-$, $-SO(CH_2)_3-$, $-SO(CH_2)_4-$, $-SO(CH_2)_5-$, $-N(Me)CH_2-$, $-SO_2CH_2-$, $-SO_2(CH_2)_2-$, $-SO_2(CH_2)_3-$, $-SO_2(CH_2)_4-$, $-SO_2(CH_2)_5-$, $-N(Me)(CH_2)_2-$, $-N(Me)(CH_2)_3-$, $-N(Me)(CH_2)_4-$, $-N(Me)(CH_2)_5-$, $-CH_2-O-CH_2-$, $-CH_2-O-(CH_2)_2-$, $-CH_2-O-(CH_2)_3-$, $-(CH_2)_2-O-CH_2-$, $-(CH_2)_2-O-(CH_2)_2-$, $-(CH_2)_3-O-CH_2-$, $-(CH_2)_3-O-(CH_2)_2-$, $-CH_2-S-CH_2-$, $-CH_2-S-(CH_2)_2-$, $-CH_2-S-(CH_2)_3-$, $-(CH_2)_2-S-CH_2-$, $-(CH_2)_2-S-(CH_2)_2-$, $-(CH_2)_3-S-CH_2-$, $-(CH_2)_3-S-(CH_2)_2-$, $-CH_2-SO-CH_2-$, $-CH_2-SO-(CH_2)_2-$, $-CH_2-SO-(CH_2)_3-$, $-(CH_2)_2-SO-CH_2-$, $-(CH_2)_2-SO-(CH_2)_2-$, $-(CH_2)_3-SO-CH_2-$, $-(CH_2)_3-SO-(CH_2)_2-$, $-CH_2-SO_2-CH_2-$, $-CH_2-SO_2-(CH_2)_2-$, $-CH_2-SO_2-(CH_2)_3-$, $-(CH_2)_2-SO_2-CH_2-$, $-(CH_2)_2-SO_2-(CH_2)_2-$, $-(CH_2)_3-SO_2-CH_2-$, $-(CH_2)_3-SO_2-(CH_2)_2-$, $-CH_2-N(Me)-C_2)_2-$, $-CH_2-N(Me)-(CH_2)_2-$, $-CH_2-N(Me)-(CH_2)_3-$, $-(CH_2)_2-N(Me)-CH_2-$, $-(CH_2)_2-N(Me)-(CH_2)_2-$, $-(CH_2)_3-N(Me)-CH_2-$, and $-(CH_2)_3-N(Me)-(CH_2)_2-$.

In further embodiments, the present invention provides nitrone compounds according to formulas (I), (II) or (III) and wherein L is no atom.

In certain embodiments, the present invention provides nitrone compounds according to formulas (I), (II) or (III) and wherein $R^1$ is tert-butyl.

In certain embodiments, the present invention provides nitrone compounds according to formulas (I), (II) or (III) and wherein $R^1$ is cyclohexyl.

In certain embodiments, the present invention provides nitrone compounds according to formulas (I), (II) or (III) and wherein $R^1$ is benzyl.

Among the aryl nitrones described above by formula (I), (II) or (III), in certain embodiments W and Z are joined to form a 6-membered aryl ring.

Among the heteroaromatic nitrones described above by formula (I), (II), or (III), in certain embodiments W and Z are joined to form a 6-membered heteroaryl ring. The heteroaryl ring can be any 5- to 8-membered heteroaryl ring known to those of skill in the art. In certain embodiments, the heteroaryl ring is a pyridine, pyrimidine, furan, thiophene or pyrrole ring.

Referring to bicyclic aryl nitrones of formula (I), (II) or (III), in certain embodiments $R^1$ is substituted with a group other than phenyl, substituted phenyl or methyl. In other embodiments $R^1$ is substituted with a group other than phenyl, substituted phenyl or lower alkyl. For instance, $R^1$ can be substituted or unsubstituted heteroalkyl, substituted or unsubstituted alkyl, substituted or unsubstituted heteroaryl, substituted or unsubstituted aralkyl, or substituted or unsubstituted heteroaralkyl.

Also referring to bicyclic aryl nitrones of formula (I), (II) or (III), in certain embodiments $R^2$ can be substituted with a group other than hydrogen. For instance, $R^2$ can be substituted or unsubstituted ($C_1$-$C_6$)alkyl, substituted or unsubstituted ($C_1$-$C_6$)cycloalkyl, substituted or unsubstituted aryl, or substituted or unsubstituted aralkyl.

Referring again to bicyclic aryl nitrones of (I), (II) or (III), in certain embodiments W and Z are joined to form a six-membered ring that is fused to a second ring. The second ring can be, for instance, a five- or six-membered ring and can contain heteroatom(s). The second ring can be fused to any adjacent pair of atoms in the first ring.

Also referring to bicyclic aryl nitrones of formulas (I), (II) or (III), in certain embodiments W and Z are joined to form a seven-membered ring that is fused to a second ring. The second ring can be, for instance, a five-membered ring and can contain heteroatom(s). The second ring can be fused to any adjacent pair of atoms in the first ring. For example, the bicyclic aromatic ring can be azulene.

In certain embodiments of aryl and heteroaromatic nitrones of formula (I), (II) or (III), W and X of Cy is C—$R^6$. While the $R^6$ substituents at W and X can vary independently, in certain embodiments both $R^6$s are identical. In particular embodiments, $R^6$ are identical when it is $SO_2R^7$ or $SO_3H$.

Among the nitrone compounds of formulas (I), (II) or (III) in certain embodiments $R^2$ is hydrogen, alkyl, heteroalkyl, aralkyl or aryl, with or without further substitution. In some embodiments, $R^2$ is hydrogen.

In some embodiments, one or more of the $R^5$ groups are hydrogen.

In some embodiments, $R^6$ is hydrogen, —$SR^7$, —$SO_2R^7$, —$SO_2NR^7R^8$, —$SO_3R^7CONR^7R^8$, —$NR^7R^8$, —OH, and —$CO_2R^7$. In certain embodiments, $R^6$ is hydrogen, —$SO_2R^7$, —$SO_2NR^7R^8$, —$SO_3R^7$, —$CONR^7R^8$, and —$CO_2R^7$.

In the heteroaromatic nitrone compounds of the invention, the atom designated by X can be substituted or unsubstituted, especially in compounds where X is a carbon or a heteroatom with a free valence. In certain embodiments, X can be substituted with any group other than hydrogen. For instance, X can be substituted with —$SR^7$, —$SO_2R^7$, —$SO_2NR^7R^8$, —$SO_3R^7$, —$CONR^7R^8$, —$NR^7R^8$, —OH, —$PO(OR^7)NR^8R^9$, —$PO(OR^7)_2$ or —$CO_2R^7$.

Referring to heteroaromatic nitrone compounds of formulas (I), (II) or (III), in some embodiments for Cy the six-membered heteroaryl ring contains one nitrogen atom, and in other embodiments the heteroaryl ring contains two nitrogen atoms. In further embodiments, the ring contains three nitrogen atoms.

When the heteroaryl ring (Cy) of formulas (I), (II) or (III) contains two nitrogen atoms, the two nitrogen atoms can be at any of W, X, Y and Z. For instance, the two nitrogen atoms can be at W and X, at W and Y, at W and Z, at X and Y, at X and Z, or at Y and Z.

Among the bicyclic aryl nitrone compounds described by formulas (I), (II) or (III), in certain embodiments W and Z are joined to form a 6-membered aryl or heteroaryl ring fused to a 5- or 6-membered cycloalkyl, cycloheteroalkyl, aryl or heteroaryl ring.

Also among the bicyclic aryl nitrone compounds of the formulas above, in some embodiments $R^1$ is alkyl, cycloalkyl, aryl or aralkyl. In certain embodiments, $R^1$ is alkyl, including lower alkyl. In certain embodiments, the lower alkyl has branching at the 1-position carbon, for example, cyclopropyl, isopropyl, sec-butyl, tert-butyl, cyclobutyl, 1-methylcycloprop-1-yl, sec-pentyl, tert-pentyl, cyclopentyl, 1-methylcyclobut-1-yl and the like. In certain embodiments, $R^1$ is tert-butyl.

In some embodiments, $R^2$ is hydrogen, alkyl, heteroalkyl, aralkyl or aryl, with or without further substitution.

In some embodiments, one or more $R^5$ groups are hydrogen.

In some embodiments, $R^6$ is hydrogen, —$SR^7$, —$SO_2R^7$, —$SO_2NR^7R^8$, —$SO_3R^7$, —$CONR^7R^8$, —$NR^7R^8$, —OH, and —$CO_2R^7$. In certain embodiments, $R^6$ is hydrogen, —$SO_2R^7$, —$SO_2NR^7R^8$, —$SO_3R^7$, —$CONR^7R^8$, and —$CO_2R^7$.

In the bicyclic aryl nitrone compounds of the invention, the atom designated by X can be substituted or unsubstituted, especially in compounds where X is a carbon or a heteroatom with a free valence. In certain embodiments, X can be substituted with any group other than hydrogen. For instance, X can be substituted with hydrogen, —$SR^7$, —$SO_2NR^7R^8$, —$SO_3R^7$, —$CONR^7R^8$, —$NR^7R^8$, —OH, —$PO(OR^7)NR^8R^9$, —$PO(OR^7)_2$, or —$CO_2R^7$.

In certain embodiments, when the compound is formula (I), L is no atom, $R^1$ is tert-butyl, $R^2$ is hydrogen, and Cy is

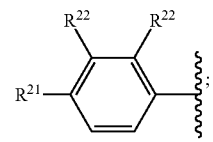

wherein
$R^{21}$ is $R^{22}$ or $R^{22}$—S—, and
each $R^{22}$ is independently selected from the group consisting of hydrogen, substituted or unsubstituted alkyl, substituted or unsubstituted aryl, substituted or unsubstituted aralkyl, substituted or unsubstituted cycloalkyl, substituted or unsubstituted cycloheteroalkyl, substituted or unsubstituted heteroalkyl, substituted or unsubstituted heteroaryl, and substituted or unsubstituted heteroarylalkyl.

In certain embodiments, when the compound is formula (I), L is no atom, $R^1$ is tert-butyl, $R^2$ is hydrogen, and Cy is

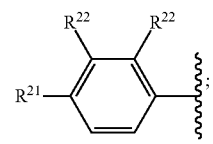

wherein $R^{21}$ is $R^{22}$—S—.

In certain embodiments, the compound is α-phenyl-tert-butyl nitrone ("PBN"), wherein the compound is formula (I), L is no atom, $R^1$ is Pert-butyl, $R^2$ is hydrogen, and Cy is a benzene.

In certain embodiments, when the compound is formula (III), the compound is symmetrical.

In certain embodiments, when the compound is formula (III), L is no atom, $R^1$ is tert-butyl, $R^2$ is hydrogen, and Cy is

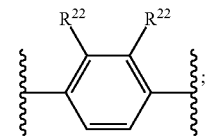

wherein
each $R^{22}$ is independently selected from the group consisting of hydrogen, substituted or unsubstituted alkyl, substituted or unsubstituted aryl, substituted or unsubstituted aralkyl, substituted or unsubstituted cycloalkyl, substituted or unsubstituted cycloheteroalkyl, substituted or unsubstituted heteroalkyl, substituted or unsubstituted heteroaryl, and substituted or unsubstituted heteroarylalkyl. Compounds of this embodiment have the following structure:

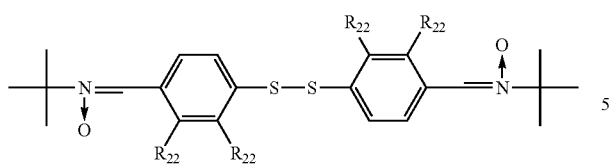

and derivatives thereof, such as the salts, solvates, hydrates, and prodrug forms thereof, and spatial isomers thereof, as well as pharmaceutical preparations thereof.

In certain embodiments, when the thiol-modified nitrone compound is a symmetrical disulfide conjugate of alpha-(4-sulfanylphenyl)-N-tert-butylnitrone, the compound is of formula (III), wherein L is no atom, $R^1$ is tert-butyl, $R^2$ is hydrogen, and Cy is benzene, (also referred to herein as TK-115339), as shown below:

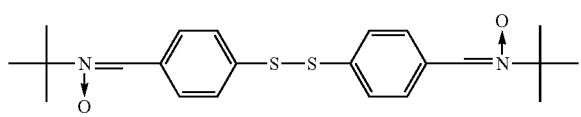

and derivatives thereof, such as the salts, solvates, hydrates, and prodrug forms thereof, and stereoisomers thereof, as well as pharmaceutical preparations thereof.

Thus in certain embodiments, the nitrone compounds are thiol-modified nitrone compounds, such as the disulfide conjugates depicted in formula (III), as well as certain compounds of formula (I) wherein Cy comprises a thiol group or thiol conjugate thereof, such as with compounds of formula (II).

By "thiol conjugate" is intended any compound or molecule capable of conjugation to a thiol group. Examples of thiol conjugates include, but are not limited to, compounds or molecules that react with the thiol to form a bond selected from disulfide, thioether, thioacetal and thioester (see, e.g., "March's Advanced Organic Chemistry: Reactions, Mechanisms, and Structure, 6th Edition," Michael B. Smith, Jerry March, 2007, John Wiley & Sons Inc.). This includes thiol protecting groups (see, e.g., "Greene's Protective Groups in Organic Synthesis, 4th Edition," Theodora W. Greene, Peter G. M. Wuts, 2006, John Wiley & Sons Inc; and "March's Advanced Organic Chemistry: Reactions, Mechanisms, and Structure, 6th Edition," Michael B. Smith, Jerry March, 2007, John Wiley & Sons Inc.). Of specific interest are thiol-modified nitrone compounds that are disulfide conjugates of formula (I).

In certain embodiments, when the thiol-modified nitrone compound is formula (I), Cy is RS-Cy, and is a compound of formula (II), wherein $R^1$, $R^2$, L and Cy are as defined above, and R is hydrogen or a thiol conjugate.

In certain embodiments, when the thiol-modified nitrone compound is formula (II), Cy is

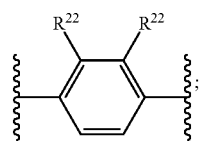

wherein $R^{22}$ is as defined above.

In certain embodiments, when the thiol-modified nitrone compound is formula (II), L is no atom, $R^1$ is tert-butyl, $R^2$ is hydrogen, and Cy is

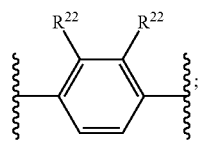

wherein $R^{22}$ is as defined above. Compounds of this embodiment have the following structure:

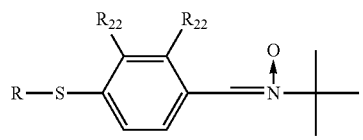

and derivatives thereof, such as the salts, solvates, hydrates, and prodrug forms thereof, and spatial isomers thereof, as well as pharmaceutical preparations thereof.

In certain embodiments, when the thiol-modified nitrone compound is formula (II), L is no atom, $R^1$ is tert-butyl, $R^2$ is hydrogen, and Cy is

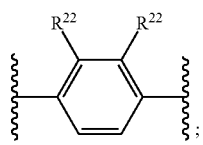

wherein each $R^{22}$ is hydrogen. Compounds of this embodiment have the following structure:

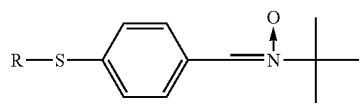

and derivatives thereof, such as the salts, solvates, hydrates, and prodrug forms thereof, and spatial isomers thereof, as well as pharmaceutical preparations thereof.

In certain embodiments, when the thiol-modified nitrone compound is formula (II), R is $R^{22}$.

In certain embodiments, when the thiol-modified nitrone compound is alpha-(4-sulfanylphenyl)-N-tert-butylnitrone, the compound is of formula (II), wherein L is no atom, $R^1$ is tart-butyl, $R^2$ is hydrogen, Cy is benzene, and R is hydrogen, as shown below:

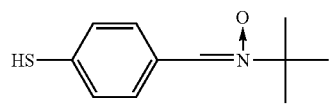

and derivatives thereof, such as the salts, solvates, hydrates, and prodrug forms thereof, and spatial isomers thereof, as well as pharmaceutical preparations thereof.

In certain embodiments of compounds of formula (II), the thiol-modified nitrone compound is an non-symmetrical disulfide conjugate of alpha-(4-sulfanylphenyl)-N-tert-butylnitrone, such as shown below.

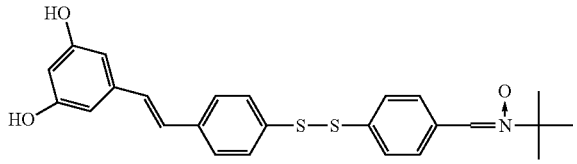 [SMILES: CC(C)(C)[N+]([O-])=Cc1ccc(SSc2ccc(/C=C/c3cc(O)cc(O)c3)cc2)cc1]

In this example, the thiol-modified nitrone is coupled to a modified resveratrol, another potent anti-oxidant with anti-inflammatory, anti-cancer and neuroprotective effects (Rocha-González et al., CNS Neurosci Ther., 14: 234-47 (2008); Rhone M et al., Nutr Rev., 66: 465-72 (2008); Udenigwe et al., Nutr Rev, 66: 445-54 (2008); Fan et al., Int J Vitam Nutr Res.; 78: 3-8 (2008); Calabrese et al., Bellia et al., Neurochem Res., 33: 2444-71 (2008); Singletary and Milner, Cancer Epidemiol Biomarkers Prev., 17:1596-610 (2008); Jiang, Biochem Biophys Res Commun., 373, 341-4 (2008); Kundu and Surh, Cancer Lett., 269, 243-61 (2008); Raval et al., Curr Med. Chem.; 15, 1545-51 (2008)).

Another embodiment is a non-symmetrical disulfide conjugate of alpha-(4-sulfanylphenyl)-N-tert-butylnitrone with an anti-thrombolytic/anti-inflammatory, such as salicylic acid as shown below.

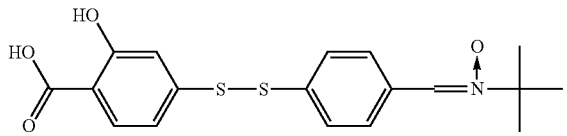 [SMILES: CC(C)(C)[N+]([O-])=Cc1ccc(SSc2ccc(C(=O)O)c(O)c2)cc1]

Thus in certain embodiments, the nitrone compounds are thiol-modified nitrone compounds, such as the disulfide conjugates, symmetrical and non-symmetrical disulphides, depicted in formulas (II) and (III), as well as certain compounds of formula (I) wherein Cy comprises a thiol group or thiol conjugate thereof. For example, nitrone compounds of formula (II) in which R is a thiol conjugate, and consisting of Cy substituted with $R^1$, $R^2$ and/or L as defined above, the thiol conjugate moiety is often an established pharmacophore or an agent added to modify clearance or distribution of the molecule. In some embodiments, such as for certain non-symmetrical disulphides of formula (II) or (III), the compound coupled to the thiol group of the nitrone-containing moiety (e.g., alpha-(4-sulfanylphenyl)-N-tert-butylnitrone) can be biologically active itself, or biologically inactive, provided only to modulate or otherwise improve or optimize one or more of the biopharmaceutical or pharmacokinetic (i.e., absorption, distribution, metabolism, and/or excretion) characteristics of the compound.

As can be appreciated, derivatives of the above compounds include not only the salts, solvates, hydrates, and prodrug forms thereof, and spatial isomers such as stereoisomers and geometric isomers thereof, as well as pharmaceutical preparations thereof, suitable derivatives include detectably labeled versions of the subject nitrone compounds, which can be radiolabels, fluorophores, luminophores, and the like. For instance, thiol-conjugates include detectable labels attached to a thiol group of the subject thiol-modified nitrone compounds of the invention, and chemistries and labels for incorporation or attachment to thiol groups are well known and commercially available.

The nitrone compounds described above and other nitrone derivatives are commercially available or can be conventionally prepared by techniques known to one of skill in the art. The compounds of formula (II) or (III) can be synthesized by coupling thiolated nitrones or other suitable coupling groups. For example, representative patents describing various nitrone compounds and derivatives thereof, as well as the synthesis/preparation thereof, include U.S. Pat. Nos. 3,849,934; 4,596,874; 4,661,433; 4,758,669; 5,025,032; 5,036,097; 5,091,449; 5,310,620; RE35,112; 5,475,032; 5,488,145; 5,498,778; 5,508,305; RE35,213; 5,723,502; 5,780,510; 5,849,771; 5,900,227; 5,942,507; 5,972,977; 5,998,469; 6,015,831; 6,034,250; 6,040,444; 6,051,571; 6,083,988; 6,083,989; 6,127,408; 6,140,356; 6,194,461; 6,197,825; 6,197,826; 6,258,852; 6,291,702; 6,310,092; 6,342,523; 6,376,540; 6,545,056; 6,569,902; 6,730,700; 6,762,322; 6,815,459; 6,835,754; and 6,998,419; as well as published U.S. Application Pub. Nos. 2005/0059638, 2005/0182060, 2005/0192281, and 2006/0100289; the disclosures of which are herein incorporated by reference.

The doxorubicin toxicity-reducing adjuvants of interest can also include a nitrone compound in conjunction with a bisdioxopiperazine compound, and be employed in a pharmaceutical composition, kit or method of the invention. For example, one such method involves administering an effective amount of a doxorubicin active agent in conjunction with an effective amount of a doxorubicin toxicity-reducing adjuvant, where the doxorubicin toxicity-reducing adjuvant includes (i) a nitrone compound or derivative thereof, and (ii) as an optional separate or admixed component, a bisdioxopiperazine compound. Thus, pharmaceutical compositions and kits for practicing this aspect of the invention also are provided.

Examples of nitrone compounds of interest are those selected from: 5,5-dimethyl-1-pyrroline-N-oxide; alpha-phenyl-N-tert-butyl nitrone; alpha-(2,4-disulfophenyl)-N-tert-butyl nitrone, alpha-(4-sulfanylphenyl)-N-tert-butylnitrone, and symmetrical disulfide conjugates of alpha-(4-sulfanylphenyl)-N-tert-butylnitrone. A nitrone compound of particular interest is alpha-phenyl-N-tert-butyl nitrone ("PBN"). Another nitrone compound of particular interest is alpha-(4-sulfanylphenyl)-N-tert-butylnitrone. Of special interest are compounds comprising alpha-(4-sulfanylphenyl)-N-tert-butylnitrone and derivatives thereof, including conjugates thereof in which the sulfanyl group is conjugated to a second compound, such as a symmetrical disulfide conjugate of alpha-(4-sulfanylphenyl)-N-tert-butylnitrone (i.e., "TK-115339"), or a non-symmetrical disulfide conjugate of alpha-(4-sulfanylphenyl)-N-tert-butylnitrone, such as alpha-(4-sulfanylphenyl)-N-tert-butylnitrone conjugated through a disulfide to a thiol-modified resveratrol or salicylic acid.

Examples of bisdioxopiperazine compounds of interest are those selected from: 4-[1-(3,5-dioxopiperazin-1-yl)propan-2-yl]piperazine-2,6-dione (dexrazoxane); 4-[1-(3,5-dioxopiperazin-1-yl)ethan-2-yl]piperazine-2,6-dione; 4-[1-(3,5-dioxopiperazin-1-yl) 1-methyl-butan-2-yl]piperazine-2,6-dione; 4-[1-(3,5-dioxopiperazin-1-yl) 1-methyl-propan-2-yl] piperazine-2,6-dione; and 4-[1-(3,5-dioxopiperazin-1-yl) butan-2-yl]piperazine-2,6-dione. A bisdioxopiperazine compound of interest is 4-[1-(3,5-dioxopiperazin-1-yl) propan-2-yl]piperazine-2,6-dione, which is also referred to as "Dexrazoxane."

In some embodiments, the nitrone compound is alpha-phenyl-N-tert-butyl nitrone (i.e., "PBN"), and the bisdioxopiperazine compound is 4-[1-(3,5-dioxopiperazin-1-yl) propan-2-yl]piperazine-2,6-dione (i.e., "Dexrazoxane"). In other embodiments, the nitrone compound is alpha-(4-sulfanylphenyl)-N-tert-butylnitrone or a non-symmetrical disulfide conjugate thereof, or a symmetrical disulfide conjugate thereof (i.e., "TK-115339"), and the bisdioxopiperazine compound is Dexrazoxane.

Dexrazoxane is a prodrug analogue of the metal chelator EDTA that protects against anthracycline-induced cardiac toxicity, and most likely acts by removing iron from the iron-doxorubicin complex, thus preventing formation of damaging reactive oxygen species (Cvetkovic et al., Drugs 65(7):1005 (2005)). The anti-tumor efficacy of anthracyclines such as doxorubicin is unlikely to be altered by dexrazoxane use ((Hochster et al., Semin Oncol. 25(4 Suppl 10):37 (1998); and Marty et al., Ann Oncol. 17(4):614 (2006)). Also, dexrazoxane appears to be useful for treating accidental extravasation injury from the use of the anthracycline anticancer drugs doxorubicin, daunorubicin, epirubicin and idarubicin, which can be a serious complication of their use (Hasinoff, B B, Future Oncol., 2(1):15-20 (2006). Accordingly, it is believed that the combination of a nitrone compound with a bisdioxopiperazine compound can further benefit a patient to reduce the unwanted side effects of doxorubicin active agents.

The bisdioxopiperazine compounds described above and other bisdioxopiperazine derivatives are commercially available or can be conventionally prepared by techniques known to one of skill in the art. For example, representative patents describing various nitrone compounds and derivatives thereof, as well as the synthesis/preparation thereof, include U.S. Pat. Nos. 3,941,790; 4,755,619; 4,764,614; 4,902,714; 4,943,578; 4,963,551; 4,963,679; 5,149,710; 5,162,372; 5,242,901; 5,278,187; 5,438,057; 5,492,913; 5,618,936; 5,688,797; 5,760,039; and 6,693,100; the disclosures of which are herein incorporated by reference. In certain embodiments, the nitrone compound is not 2,4-disulfonyl α-phenyl tertiary butyl nitrone, e.g., as disclosed in U.S. Pat. No. 5,508,305.

As indicated above, an effective amount of toxicity-reducing adjuvant is employed in the subject methods. In certain embodiments, the amount of toxicity-reducing adjuvant employed is not more than about the amount of the doxorubicin active agent employed. In certain embodiments, the amount of toxicity-reducing adjuvant employed is an amount that is less than equi-molar to the amount of doxorubicin active agent that is administered. Typically, the amount of toxicity-reducing adjuvant that is administered is less than about 75%, less than about 50%, less then about 25% and many embodiments less than about 15%, less than about 10% and even less than about 5% or 1% than the amount of doxorubicin active agent. In other embodiments, the effective amount is the same as the amount of the active agent, and in certain embodiments the effective amount is an amount that is more than the amount of the doxorubicin active agent. Effective amounts can readily be determined empirically using the data provided in the Experimental section, below.

Standard dosing regiments can be employed in which the doxorubicin toxicity-reducing adjuvant is administered within the window of therapeutic opportunity. For example, one regimen for administering a doxorubicin toxicity-reducing adjuvant is from about 6 to 12 hours before to about 6 to 12 hours after the start of a particular doxorubicin dosing regimen, such as from about 3 to 6 hours before to about 3 to 6 hours after the start of a doxorubicin dosing regimen. Thus in one embodiment, a doxorubicin toxicity-reducing adjuvant is given to a patient in need thereof within the window of therapeutic opportunity for that patient, i.e., within a few hours before or after the start of a doxorubicin dosing regimen.

Optimal dosing strategies also can be employed in which dosing is individualized based on a metabolite clearance parameter or bodyweight, estimated using the population pharmacokinetic models, empirical covariate distributions relevant for the target population, and a target definition based on target fulfillment criteria and parsimony. For instance, the doxorubicin toxicity-reducing adjuvant (as separate or combined components) can be administered as a loading dose to reach an effective plasma concentration over a short period of time, and optionally, followed by one or more subsequent (or continuous) doses to maintain the desired plasma level for a given period of time. A particular example of a loading-maintenance dose approach is where a doxorubicin toxicity-reducing adjuvant is administered as a loading dose over about 1 to 2 hours, followed by a maintenance dose(s) for about 24 to 72 hours. Thus, loading as well as maintenance or standard dosing can be individualized based on pharmacokinetic parameters, such as the monitoring clearance of a particular metabolite, in conjunction with cut-off values at which dosing amounts and rates are incremented or decremented. It will be appreciated that dosing regiment can include intermittent recovery periods, such as recovery periods between the various treatments.

The scope of the present invention includes prodrugs of the doxorubicin active agent and doxorubicin toxicity-reducing adjuvant. Such prodrugs are, in general, functional derivatives of the compounds that are readily convertible in vivo into the required compounds. Thus, in the methods of the present invention, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. *The Practice of Medicinal Chemistry*, 2d Ed., pp. 561-586 (Academic Press 2003). Prodrugs include esters that hydrolyze in vivo (e.g., in the human body) to produce a compound described herein suitable for the present invention. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates.

Formulations

Also provided are pharmaceutical compositions containing the doxorubicin active agent and/or doxorubicin toxicity-reducing adjuvant employed in the subject methods. Accordingly, the doxorubicin active agent and/or doxorubicin toxicity-reducing adjuvant can be formulated for oral or parenteral administration for use in the subject methods, e.g., in the form of a pharmaceutically acceptable salt, as described above. In certain embodiments, e.g., where the compounds are administered as separate formulations (such as in those embodiments where they are administered sequentially), separate or distinct pharmaceutical compositions, each containing a different active agent, are provided. In yet other embodiments, a single formulation that includes both of the doxorubicin active agent and/or doxorubicin toxicity-reducing adjuvant (i.e., one composition that includes both active agents) is provided.

By way of illustration, the doxorubicin active agent and/or doxorubicin toxicity-reducing adjuvant can be admixed with conventional pharmaceutically acceptable carriers and excipients (i.e., vehicles) and used in the form of aqueous solutions, tablets, capsules, elixirs, suspensions, syrups, wafers, and the like. Such pharmaceutical compositions contain, in certain embodiments, from about 0.1 to about 90% by weight of the active compound, and more generally from about 1 to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example, a powder containing active compound, suspending agent, sucrose and a sweetener can be reconstituted with water to form a suspension, and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil; for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetracetic acid, and an antioxidant, for example, sodium metabisulphite may be included in the formulation. Alternatively, the solution can be freeze dried and then reconstituted with a suitable solvent just prior to administration.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, herein incorporated by reference in its entirety). Such patches may be constructed for continuous, pulsatile, or on demand delivery of pharmaceutical agents.

In certain embodiments of interest, the doxorubicin active agent and the toxicity-reducing adjuvant are administered as a single pharmaceutical formulation, that, in addition to including an effective amount of the active agent and toxicity-reducing adjuvant, includes other suitable compounds and carriers, and also may be used in combination with other active agents. The present invention, therefore, also includes pharmaceutical compositions comprising pharmaceutically acceptable excipients. The pharmaceutically acceptable excipients include, for example, any suitable vehicles, adjuvants, carriers or diluents, and are readily available to the public. The pharmaceutical compositions of the present invention may further contain other active agents as are well known in the art.

One skilled in the art will appreciate that a variety of suitable methods of administering a formulation of the present invention to a subject or host, e.g., patient, in need thereof, are available, and, although more than one route can be used to administer a particular formulation, a particular route can provide a more immediate and more effective reaction than another route. Pharmaceutically acceptable excipients are also well-known to those who are skilled in the art, and are readily available. The choice of excipient will be determined in part by the particular compound, as well as by the particular method used to administer the composition. Accordingly, there are a wide variety of suitable formulations of the pharmaceutical composition of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art to be appropriate.

The subject formulations of the present invention can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are known in the art to be appropriate.

Suppository formulations are also provided by mixing with a variety of bases such as emulsifying bases or water-soluble bases. Formulations suitable for vaginal administration may be presented as pessaries, tampons, creams, gels, pastes, foams.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Those of skill in the art will readily appreciate that dose levels can vary as a function of the specific compound, the nature of the delivery vehicle, and the like. Suitable dosages for a given compound are readily determinable by those of skill in the art by a variety of means.

The dose administered to an animal, particularly a human, in the context of the present invention should be sufficient to elicit a prophylactic or therapeutic response in the animal over a reasonable time frame. One skilled in the art will recognize that dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound. Suitable doses and dosage regimens can be determined by comparisons to anticancer or immunosuppressive agents that are known to elicit the desired growth inhibitory or immunosuppressive response. In the treatment of some individuals with the compounds of the present invention, it may be desirable to use a high dose regimen in conjunction with a rescue agent for non-malignant cells. In such treatment, any agent capable of rescue of non-malignant cells can be employed, such as citrovorum factor, folate derivatives, or leucovorin. Such rescue agents are well known to those of ordinary skill in the art. Rescue agents include those which do not interfere with the ability of the present inventive compounds to modulate cellular function.

Optionally, the pharmaceutical composition may contain other pharmaceutically acceptable components, such a buffers, surfactants, antioxidants, viscosity modifying agents, preservatives and the like. Each of these components is well-known in the art (see, e.g., U.S. Pat. No. 5,985,310, the disclosure of which is herein incorporated by reference).

In another embodiment, the aqueous cyclodextrin solution further comprises dextrose, e.g., about 5% dextrose. Other components suitable for use in the formulations of the present invention can be found in Remington's Pharmaceutical Sciences, Mace Publishing Company, Philadelphia, Pa., 17th ed. (1985).

Utility

The subject methods find use in therapeutic applications in which doxorubicin administration is indicated. A representative therapeutic application is the treatment of cellular proliferative disease conditions, e.g., cancers and related conditions characterized by abnormal cellular proliferation concomitant. Such disease conditions include cancer/neoplastic diseases and other diseases characterized by the presence of unwanted cellular proliferation, e.g., hyperplasias, and the like. In these capacities, use of the present compositions will result in reducing unwanted toxicity while retaining the desired doxorubicin activity.

By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the side-effects of the doxorubicin treatment or at least the symptoms that characterize the side-effects.

A specific application of interest is the use of the nitrone compounds of the invention to ameliorate doxorubicin-induced cardiotoxicity. When the cumulative dose of doxorubicin reaches 450-550 mg/m$^2$, the risk of developing cardiac side effects, including congestive heart failure, dilated cardiomyopathy, and death, dramatically increase. Doxorubicin cardiotoxicity can be characterized by a dose-dependent decline in mitochondrial oxidative phosphorylation. Reactive oxygen species, generated by the interaction of doxorubicin with iron, can then damage the myocytes (heart cells), causing myofibrillar loss and cytoplasmic vacuolization. Additionally, some patients may develop "Hand-Foot Syndrome" characterized by skin eruptions on the palms of the hand or soles of the feet, characterized by swelling, pain and erythema.

Doxorubicin cardiotoxicity can also be characterized by certain subtypes of troponin (cardiac troponin I and T), which are very sensitive and specific indicators of damage to the heart muscle (myocardium). Cardiac damage results in elevated cardiac troponin levels in the blood. Thus, levels of cardiac troponin I and/or T can be easily measured in the blood or plasma to test for damaged heart muscle, including cardiac damage resulting from myocardial infarction.

Accordingly, in certain embodiments, a method is provided for the treatment of a host in need thereof an effective amount of a doxorubicin active agent in conjunction with an amount of an doxorubicin toxicity-reducing adjuvant effective to reduce doxorubicin-induced cardiotoxicity in the host, wherein the doxorubicin toxicity-reducing adjuvant is a nitrone compound of formulas (I), (II) or (III). In a related embodiment, the doxorubicin-induced cardiotoxicity is characterized by one or more features selected from decline in mitochondrial oxidative phosphorylation and an increase in cardiac troponin levels. Of interest is the use of thiol-modified nitrone compounds of formulas (I), (II) and (III), and particularly thiol-modified nitrone compounds of formulas (II) and (III), and more particularly compound TK115339, as the doxorubicin toxicity-reducing adjuvant to reduce doxorubicin-induced cardiotoxicity in the subject.

Reduction of doxorubicin-induced cardiotoxicity is characterized by the prevention, mitigation, or reduction of the likelihood of onset of cardiotoxicity resulting from treatment of a host with a doxorubicin active agent. This includes treatment of a host in need thereof with an effective amount of a doxorubicin active agent in conjunction with an amount of a doxorubicin toxicity-reducing adjuvant effective to reduce doxorubicin-induced cardiotoxicity in the host, where the doxorubicin toxicity-reducing adjuvant improves the likelihood of successfully preventing or eliminating one or more features of cardiotoxicity when it has occurred including: (i) prevention, that is, causing the clinical symptoms not to develop, e.g., preventing a decline in mitochondrial oxidative phosphorylation and/or damage to heart muscle, and/or preventing progression of one or more of these features to a harmful state; (ii) inhibition, that is, arresting the development or further development of clinical symptoms, e.g., mitigating or completely inhibiting an active (ongoing) feature of cardiotoxicity so that the feature is decreased to the degree that it is no longer seriously harmful, which decrease can include complete elimination of cardiotoxicity from the host; and/or (iii) relief, that is, causing the regression of clinical symptoms, e.g., causing a relief from a decline in mitochondrial oxidative phosphorylation and/or damage to heart muscle, and/or other symptoms caused by treatment of the host with a doxorubicin active agent.

The thiol-modified nitrone compounds of formulas (I), (II) and (III), and particularly thiol-modified nitrone compounds of formulas (II) and (III), and more particularly compound TK115339, may also find use in the treatment of other disorders amenable to nitrone compound-based therapies, such as described in U.S. Pat. Nos. 5,025,032; 5,036,097; 5,622,994; 5,780,510; 6,083,988; 6,107,315; 6,1978,25; 6,291,702; and 6,815,425.

A variety of subjects are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects will be humans.

In certain embodiments, the subjects will be subjects that have been diagnosed for and are therefore in need of administration of the active agent. In certain embodiments, the methods may include diagnosing the subject for the presence of the disease condition to be treated by administration of the active agent.

The subject methods find use in, among other applications, the treatment of cellular proliferative disease conditions, including neoplastic disease conditions, i.e., cancers. In such applications, an effective amount of a doxorubicin active agent and a doxorubicin toxicity-reducing adjuvant are administered to the subject in need thereof. Treatment is used broadly as defined above, i.e., to include at least an amelioration in one or more of the symptoms of the disease, as well as a complete cessation thereof, as well as a reversal and/or complete removal of the disease condition, i.e., a cure.

There are many disorders associated with a dysregulation of cellular proliferation, i.e., cellular hyperproliferative disorders.

Such conditions include those where there is proliferation and/or migration of smooth muscle cells, and/or inflammatory cells into the intimal layer of a vessel, resulting in restricted blood flow through that vessel, i.e. neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Other conditions of interest include diseases where there is hyperproliferation and tissue remodelling or repair of reproductive tissue, e.g. uterine, testicular and ovarian carcinomas, endometriosis, squamous and glandular epithelial carcinomas of the cervix, etc.

Tumors of interest for treatment include carcinomas, e.g. colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma, etc.; neurological malignancies, e.g. neuroblastoma, gliomas, etc.; hematological malignancies, e.g. childhood acute leukaemia, acute myelogenous leukemias, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Some cancers of particular interest include breast cancers, which are primarily adenocarcinoma subtypes. Ductal carcinoma in situ (DCIS) is the most common type of noninvasive breast cancer. In DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Another disease of interest is melanoma which is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the higher the chance of lymph node metastases and the worse the prognosis the greater the thickness and depth of local invasion of the melanoma. Melanoma can spread by local extension (through lymphatics) and/or by hematogenous routes to distant sites. Any organ may be involved by metastases, but lungs and liver are common sites.

Other hyperproliferative diseases of interest relate to epidermal hyperproliferation, tissue remodelling and repair. For example, the chronic skin inflammation of psoriasis is associated with hyperplastic epidermal keratinocytes as well as infiltrating mononuclear cells, including CD4+ memory T cells, neutrophils and macrophages.

The methods of the present invention can provide a highly general method of treating many, if not most, malignancies, including tumors derived from cells selected from skin, connective tissue, adipose, breast, lung, stomach, pancreas, ovary, cervix, uterus, kidney, bladder, colon, prostate, central nervous system (CNS), retina and blood, and the like. Representative cancers of interest include, but are not limited to: head/neck and lung tissue (e.g., head and neck squamous cell carcinoma, non-small cell lung carcinoma, and small cell lung carcinoma), gastrointestinal tract and pancreas (e.g., gastric carcinoma, colorectal adenoma, colorectal carcinoma, pancreatic carcinoma), hepatic tissue (e.g., hepatocellular carcinoma), kidney and urinary tract (e.g., dysplastic urothelium, bladder carcinoma, renal carcinoma, Wilms tumor), breast (e.g., breast carcinoma), neural tissue (e.g., retinoblastoma, oligodendroglioma, neuroblastoma, malignant meningioma, skin (e.g., normal epidermis, squamous cell carcinoma, basal cell carcinoma, melanoma, etc.), hematological tissues (e.g., lymphoma, chronic myeloid leukemia (CML), acute promyelocytic leukemia (APL), acute lymphoblastic leukemia (ALL), acute myeloid leukemia (AML), etc.), and the like.

The dose administered to an animal, particularly a human, in the context of the present invention should be sufficient to affect a prophylactic or therapeutic response in the animal over a reasonable time frame. One skilled in the art will recognize that dosage will depend on a variety of factors including the strength of the particular compound employed, the dose of doxorubicin, the dosing regimen used for doxorubicin, the condition of the animal, and the body weight of the animal, as well as the severity of the illness and the stage of the disease.

The size of the dose will also be determined by the existence, nature, and extent of any adverse side-effects that might accompany the administration of a particular compound.

Particular applications in which the subject methods and compositions find use include those described in U.S. Pat. Nos. 6,251,355; 6,224,883; 6,130,245; 6,126,966; 6,077,545; 6,074,626; 6,046,044; 6,030,783; 6,001,817; 5,922,689; 4,322,391; and 4,310,515; the disclosures of which are herein incorporated by reference.

Additional applications in which the subject combination of doxorubicin active agent and doxorubicin toxicity-reducing adjuvant find use include those described further in U.S. Pat. No. 6,541,506 (such as coating of medical instruments or implants, agricultural applications, etc.) the disclosure of which is herein incorporated by reference.

Kits & Systems

Also provided are kits and systems that find use in practicing the subject methods, as described above. For example, kits and systems for practicing the subject methods may include one or more pharmaceutical formulations, which include one or both of the doxorubicin active agent and doxorubicin toxicity-reducing adjuvant. As such, in certain embodiments the kits may include a single pharmaceutical composition, present as one or more unit dosages, where the composition includes both the doxorubicin active agent and doxorubicin toxicity-reducing adjuvant. In yet other embodiments, the kits may include two or more separate pharmaceutical compositions, each containing either a doxorubicin active agent or a doxorubicin toxicity-reducing adjuvant.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., a diskette, a CD, etc., on which the information has been recorded. Yet another means that may be present is a website address which may be used via the internet to access the information at a remote site. Any convenient means may be present in the kits.

The term "system" as employed herein refers to a collection of a doxorubicin active agent and a doxorubicin toxicity-reducing adjuvant, present in a single or disparate composition, that are brought together for the purpose of practicing the subject methods. For example, separately obtained doxorubicin active agent and doxorubicin toxicity-reducing adjuvant dosage forms brought together and co-administered to a subject, or administered sequentially, or administered as part of another treatment regimen, according to the present invention, are a system according to the present invention.

The following examples further illustrate the present invention and should not be construed as in any way limiting its scope.

EXPERIMENTAL RESULTS

I. Mouse Study

The efficacy of cancer chemotherapy can be improved if agents are available to minimize the adverse events associated with treatment with cytotoxics. The aim of this study was to find a dose of a nitrone compound that protects against doxorubicin-induced toxicity in a mouse.

To this end, a representative nitrone test article (TK-115339) was examined for its ability to mitigate one aspect of doxorubicin-induced toxicity, cardiac damage, in CD-1 mice as determined by concentration of cardiac troponin I (cTnI) in animal plasma (Li et al., Circulation, 113:535-43 (2006) and Hou et al., J Lab Clin Med., 146: 299-303 (2005). Doxorubicin was purchased from Xinchem Corporation (China). TK-115339 was synthesized at the University of California, Santa Cruz.

Eight to ten-week-old male CD-1 male mice (Charles River, Hollister, Calif.) weighing 20-25 g were housed in a climate-controlled environment, the light was controlled (light:dark, 12:12), and the animals given food and water ad libitum. The animals (10 animals/treatment group) were dosed ip (200 µl volume) on day 1 with vehicle (pH 7.4 buffered saline), 25 mg/kg doxorubicin or 25 mg/kg doxorubicin plus 1.0 or 3.0 mg/kg TK-115339 3 hours before, and after, the doxorubicin treatment. A 1 mL syringe and 27G1/2 needle was used for the injection, and the total injection volume of either doxorubicin or TK-115339 was 200 µL.

On days 2, 3 and 4, the mice received a single ip injection of either 1 or 3 mg/kg of TK-115339. On day 5 (96-hours post initial dosing with doxorubicin), plasma samples were obtained from each animal by retro-orbital puncture using a 75 mm untreated plastic clad Hematocrit tube. The mice were then euthanized by carbon dioxide suffocation. The plasma samples were analyzed for cTnI using a commercial ELISA test according to the manufacture's recommendations (Life Diagnostics, Inc., Cat. No. 2010-1-HSP).

Data was analyzed using SPSS software (SPSS Inc., Chicago, Ill.). The Mann-Whitney U test was used for comparison of population variances followed by an independent samples T test.

A representative set of data is depicted in FIG. 1, which demonstrates that TK-115339 protects mice from doxorubicin-induced cardiac damage estimated by measurement of plasma cardiac troponin. Representative of the data shown in FIG. 1, mice (10 animals/treatment group) were dosed ip on Day 1 with vehicle (pH 7.4 buffered saline), 25 mg/kg doxorubicin ip or 25 mg/kg doxorubicin ip plus 1.0 or 3.0 mg/kg TK-115339 3 hours before, and after, the doxorubicin treatment. On days 2, 3 and 4, the mice received a single ip injection of either 1 or 3 mg/kg of TK-115339. On Day 5 (96-hours post initial dosing with doxorubicin), plasma samples were obtained from each animal by retro-orbital eye bleeds and the mice sacrificed. The plasma samples were analyzed for cTnI using a commercial ELISA test for troponin I. Boxplots of troponin findings from the study are provided in FIG. 1.

II. Mouse Dose Response Study

The aim of this study was to establish the dose response for the protection afforded by TK-115339 against doxorubicin-associated cardiotoxicity.

Eight to ten-week-old male CD-1 male mice (Charles River, Hollister, Calif.) weighing 30-35 g were housed in a climate-controlled environment, the light was controlled (light:dark, 12:12), and the animals were given food and water ad libitum. The animals (12 animals/treatment group) were dosed ip (200 µl volume) on day 1 with 25 mg/kg doxorubicin or 25 mg/kg doxorubicin plus 0.0001, 0.001, 0.01, 0.1 or 1.0 mg/kg TK-115339 3 hours before, and after, the doxorubicin treatment. A 1 mL syringe and 27G1/2 needle was used for the injection, and the total injection volume of either doxorubicin or TK-115339 was 200 µL.

On days 2 and 3 the mice received a single ip injection of either saline (doxorubicin alone group) or TK-1153393 (dose ranging experimental groups). On day 5 (96-hours post initial dosing with doxorubicin), plasma samples were obtained from each animal by retro-orbital puncture using a 75 mm untreated plastic clad Hematocrit tube. The mice were then euthanized by carbon dioxide suffocation. The plasma samples were analyzed for cTnI using a commercial ELISA test according to the manufacture's recommendations (Life Diagnostics, Inc., Cat. No. 2010-1-HSP).

Data was analyzed using SPSS software (SPSS Inc., Chicago, Ill.). The Mann-Whitney U test was used for comparison of population variances followed by an independent samples T test.

Figure 2:
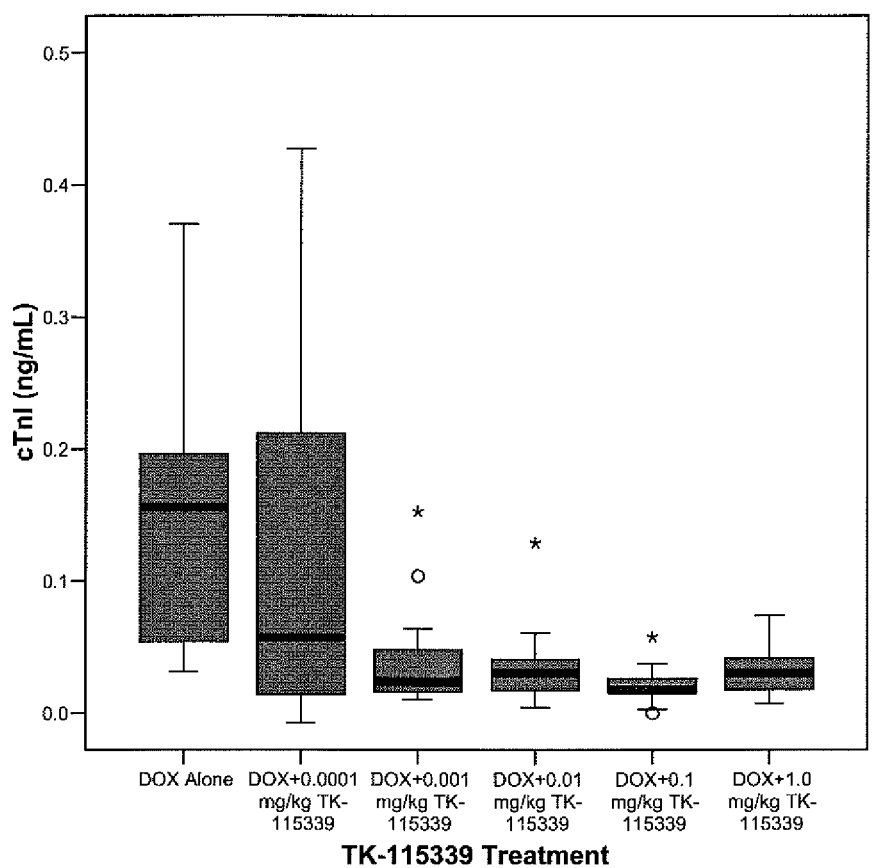
FIG. 2 depicts a set of data demonstrating a dose-response for the protection afforded by TK-115339 against doxorubicin-induced toxicity.

A representative set of data are depicted in FIG. 2, which demonstrates the protection afforded by TK-115339 from doxorubicin-induced cardiac damage, estimated by measurement of plasma cardiac troponin, is dose proportional. Representative of the data shown in FIG. 2, mice (12 animals/treatment group) were dosed ip on Day 1 with 25 mg/kg doxorubicin or 25 mg/kg doxorubicin plus 0.0001, 0.001, 0.01, 0.1 or 1.0 mg/kg TK-115339 3 hours before, and after, the doxorubicin treatment. On Day 5 (96-hours post initial dosing with doxorubicin), plasma samples were obtained from each animal by retro-orbital eye bleeds and the mice sacrificed. The plasma samples were analyzed for cTnI using a commercial ELISA test. Boxplots of troponin findings from the study are provided in FIG. 2.

III. Cell Culture Study

The aim of this study was to examine whether or not a representative nitrone test article, TK-115339, interfered with the desired activity of doxorubicin in vitro.

The tumor cell line for the cell culture study was CCRF-CEM (Human T-ALL, CCL-119) from ATCC, and cells were cultured in accordance with the product information sheets replacing 75 $cm^2$ culture flasks with 56.7 $cm^2$ Petri dishes and adding 1% penicillin-streptomycin solution and 1% GlutaMAX™ to the culture medium. The compound, TK-115339, was dissolved in DMSO then diluted to obtain initial working solutions of 1, 10 and 100 µM. In testing, 100-fold dilutions were made in culture media to give final assay concentrations of 0.01, 0.1 and 1.0 µM. Doxorubicin was dissolved in sterile filtered PBS. Three 100× solutions were made to give final assay concentrations of 0.01, 0.1 and 1.0 µM.

Cells were thawed according to ATCC protocol and plated in 10 mL of sterile filtered growth medium. Cells were sub-cultured 3 to 7 times before starting the experiments. The cell suspension was diluted during the logarithmic growth phase at a ratio of 1 mL of cell suspension to 4 mL of fresh growth media. Aliquots of 100 µL of this suspension were plated in 96 well microtiter plates and grown under ATCC recommended atmospheric conditions. After 24 hours, 100 µL of growth medium and 2 µL of test solution were added to each well for 72 hour incubation. Doxorubicin was evaluated at concentrations of 0.01, 0.1 and 1.0 µM alone or in combination with TK-115339 at concentrations of 0.01, 0.1 and 1.0 µM. In addition, the same concentrations of TK-115339 were tested alone. For each condition, n=12.

At the end of incubation, cell viability was determined by optical absorbance of alamarBlue® at λ=570 and 600 nm in accordance using a standard protocol provided by the vendor, Biosource. Data was analyzed using SPSS 14.0 software (SPSS Inc., Chicago, Ill.). Statistical significance of the differences between experimental groups was calculated by using one-way ANOVA followed by a Bonferroni post-hoc analysis.

Figure 3:
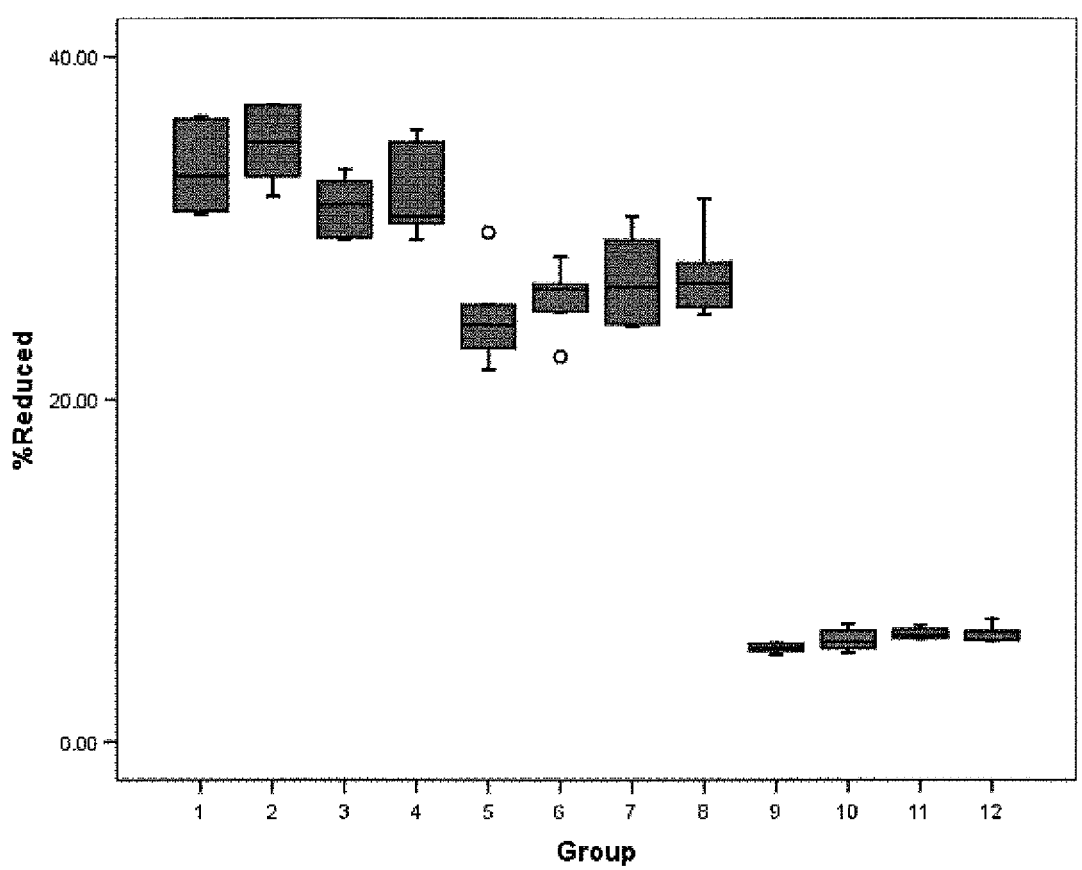
FIG. 3 depicts a set of data demonstrating that TK-115339 does not interfere with the toxicity of doxorubicin in CCRF-CEM human cancer cells.

Boxplots of typical results are provided in FIG. 3, which demonstrates that TK-115339 does not interfere with the tumor cell anti-growth activity of doxorubicin. Cells were prepared and tested as described above. Doxorubicin was evaluated at concentrations of 0.01, 0.1 and 1.0 µM alone or in combination with TK-115339 at concentrations of 0.01, 0.1 and 1.0 µM. TK-115339 was also tested alone at concentrations of 0.01, 0.1 and 1.0 µM. For each condition, 12 replicates were analyzed. At the end of incubation, cell viability was determined by alamarBlue® using optical absorbance measurements at λ=570 and 600 nm. As shown in FIG. 3 (Group 1=doxorubicin 0.01 µM; Group 2-4=doxorubicin 0.01 µM+TK-115339 at 0.01, 0.1, and 1.0 µM; Groups 5=doxorubicin 0.1 µM; Group 6-8=doxorubicin 0.1 µM+TK-115339 at 0.01, 0.1, and 1.0 µM; Group 9=doxorubicin 1.0 µM; Groups 10-12=doxorubicin 1.0 µM+TK-115339 at 0.01, 0.1, and 1.0 µM), TK-115339, a representative nitrone test article, does not interfere with the desired cytotoxicity of doxorubicin. Taken together with the animal data, it is evident that nitrone compounds such as TK-115339 are capable of reducing doxorubicin-induced toxicity while not significantly impacting the beneficial anti-neoplastic activity of doxorubicin.

It is evident from the above results and discussion that the subject invention provides for methods of reducing the unwanted toxicity of doxorubicin active agents while retaining their desired activity. As such, the subject invention finds use in a variety of different applications and represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of administering to a subject in need thereof an effective amount of a doxorubicin active agent, said method comprising:
   simultaneously administering to said subject said effective amount of a doxorubicin active agent that is an anthracycline antibiotic in conjunction with an amount of a doxorubicin toxicity-reducing adjuvant effective to reduce toxicity of said doxorubicin active agent, wherein said doxorubicin toxicity-reducing adjuvant is a nitrone compound of formula (II):

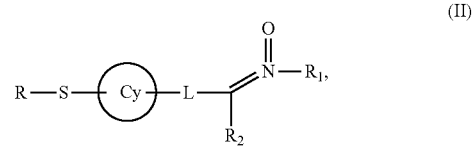

or a pharmaceutically acceptable salt thereof, or a spatial isomer thereof;

wherein:

R is hydrogen or a disulfide conjugate;

L is $-[C(R^3)_2]_m-X'-[C(R^4)_2]_n-$; m is an integer from 0 to 6; n is an integer from 0 to 6;

X' is selected from the group consisting of no atom, $NR_2$, O, S, SO and $SO_2$;

Cy is selected from the group consisting of substituted or unsubstituted cycloalkyl, substituted or unsubstituted aryl, substituted or unsubstituted heteroaryl, substituted or unsubstituted cycloheteroalkyl, bicycloalkenyl, bicycloheteroalkenyl, bicycloaryl, or bicycloheteroaryl ring;

$R^1$ is selected from the group consisting of substituted or unsubstituted aliphatic, substituted or unsubstituted alkyl, substituted or unsubstituted heteroalkyl, substituted or unsubstituted aryl, substituted or unsubstituted heteroaryl, substituted or unsubstituted aralkyl, and substituted or unsubstituted heteroaralkyl;

$R^2$ is selected from the group consisting of hydrogen, substituted or unsubstituted alkyl, substituted or unsubstituted cycloalkyl, substituted or unsubstituted aryl, substituted or unsubstituted heteroaryl, and substituted or unsubstituted aralkyl;

$R^3$ is selected from the group consisting of hydrogen, substituted or unsubstituted alkyl, substituted or unsubstituted cycloalkyl, substituted or unsubstituted aryl, substituted or unsubstituted heteroaryl, and substituted or unsubstituted aralkyl;

$R^4$ is selected from the group consisting of hydrogen, substituted or unsubstituted alkyl, substituted or unsubstituted cycloalkyl, substituted or unsubstituted aryl, and substituted or unsubstituted aralkyl, and any two $R^3$s may join together to form a cycloalkyl, cycloheteroalkyl ring; and one of $R^3$s and one of $R^4$s on carbon atoms adjacent to X' may join together to form a heterocyclic ring of 5-7 atoms.

2. The method according to claim 1, wherein R is a disulfide conjugate, and said compound is of formula (III):

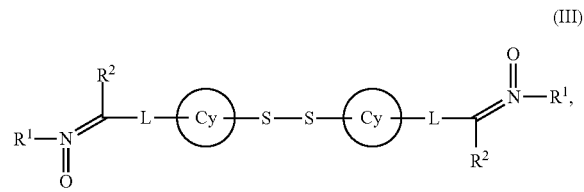

wherein $R^1$, $R^2$, L and Cy are each individually the same or different, and wherein said compound is symmetrical or non-symmetrical.

3. The method according to claim 1, wherein L is no atom, $R^1$ is tert-butyl, $R^2$ is hydrogen, and Cy is

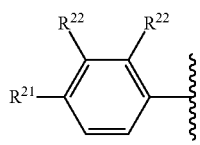

wherein

R²¹ is R²²—S—, and each R²² is independently selected from the group consisting of hydrogen, substituted or unsubstituted alkyl, substituted or unsubstituted alkyl, substituted or unsubstituted arylalkyl, substituted or unsubstituted cycloalkyl, substituted or unsubstituted cycloheteroalkyl, substituted or unsubstituted heteroalkyl, substituted or unsubstituted heteroaryl, and substituted or unsubstituted heteroarylalkyl.

4. The method according to claim 3, wherein each R²² is hydrogen.

5. The method according to claim 2, wherein L is no atom, R¹ is tert-butyl, R² is hydrogen, and Cy is

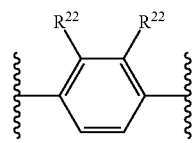

wherein each R²² is independently selected from the group consisting of hydrogen, substituted or unsubstituted alkyl, substituted or unsubstituted alkyl, substituted or unsubstituted arylalkyl, substituted or unsubstituted cycloalkyl, substituted or unsubstituted cycloheteroalkyl, substituted or unsubstituted heteroalkyl, substituted or unsubstituted heteroaryl, and substituted or unsubstituted heteroarylalkyl.

6. The method according to claim 5, wherein each R²² is independently selected from the group consisting of hydrogen and hydroxyl.

7. The method according to claim 1, wherein R is a disulfide conjugate that can be biologically active or biologically inactive, and is capable of modulating one or more of the biopharmaceutical and/or pharmacokinetic characteristics of said compound.

8. The method according to claim 1, wherein said compound is selected from the group consisting of:

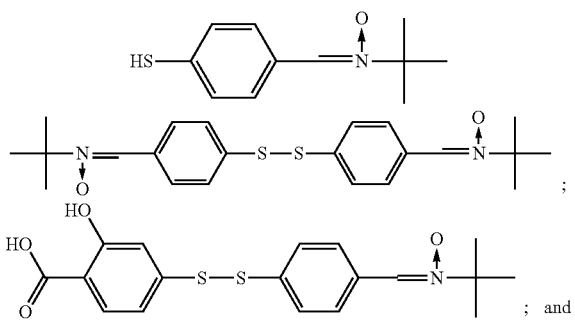

-continued

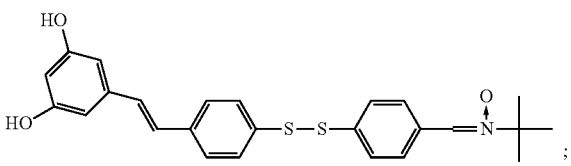

or the pharmaceutically acceptable salts, solvates, hydrates, and prodrug forms thereof, spatial isomers thereof.

9. A composition comprising a thiol-modified nitrone compound of formula (II):

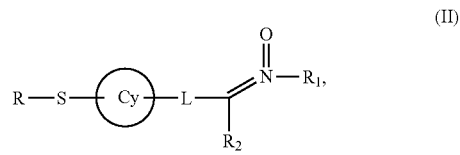

(II)

or a salt thereof, or a spatial isomer thereof;

wherein R is hydrogen, or a disulfide conjugate;

L is —[C(R³)₂]$_m$—X'—[C(R⁴)₂]$_n$—; m is an integer from 0 to 6; n is an integer from 0 to 6;

X' is selected from the group consisting of no atom, NR₂, O, S, SO and SO₂;

Cy is selected from the group consisting of substituted or unsubstituted cycloalkyl, substituted or unsubstituted aryl, substituted or unsubstituted heteroaryl, substituted or unsubstituted cycloheteroalkyl, bicycloalkenyl, bicycloheteroalkenyl, bicycloaryl, or bicycloheteroaryl ring;

R¹ is selected from the group consisting of substituted or unsubstituted aliphatic, substituted or unsubstituted alkyl, substituted or unsubstituted heteroalkyl, substituted or unsubstituted aryl, substituted or unsubstituted heteroaryl, substituted or unsubstituted aralkyl, and substituted or unsubstituted heteroaralkyl; and R² is selected from the group consisting of hydrogen, substituted or unsubstituted alkyl, substituted or unsubstituted cycloalkyl, substituted or unsubstituted aryl, substituted or unsubstituted heteroaryl, and substituted or unsubstituted aralkyl each R³ is independently selected from the group consisting of hydrogen, substituted or unsubstituted alkyl, substituted or unsubstituted cycloalkyl, substituted or unsubstituted aryl, substituted or unsubstituted heteroaryl, and substituted or unsubstituted aralkyl;

each R⁴ is independently selected from the group consisting of hydrogen, substituted or unsubstituted alkyl, substituted or unsubstituted cycloalkyl, substituted or unsubstituted aryl, and substituted or unsubstituted aralkyl, and any two R³s may join together to form a cycloalkyl, cycloheteroalkyl ring;

and one of R³s and one of R⁴s on carbon atoms adjacent to X' may join together to form a heterocyclic ring of 5-7 atoms.

10. The composition according to claim 9, wherein R is a disulfide conjugate, and said compound is of formula (III):

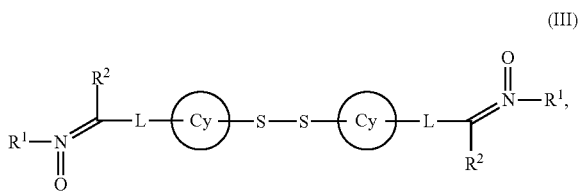

wherein:

L is —[C(R³)₂]ₘ—X—[C(R⁴)₂]ₙ—; m is an integer from 0 to 6; n is an integer from 0 to 6;

X' is selected from the group consisting of no atom, NR₂, O, S, SO and SO₂;

each Cy is independently selected from the group consisting of substituted or unsubstituted cycloalkyl, substituted or unsubstituted aryl, substituted or unsubstituted heteroaryl, substituted or unsubstituted cycloheteroalkyl, bicycloalkenyl, bicycloheteroalkenyl, bicycloaryl, or bicycloheteroaryl ring;

each R¹ is independently selected from the group consisting of substituted or unsubstituted aliphatic, substituted or unsubstituted alkyl, substituted or unsubstituted heteroalkyl, substituted or unsubstituted aryl, substituted or unsubstituted heteroaryl, substituted or unsubstituted aralkyl, and substituted or unsubstituted heteroaralkyl;

each R² is independently selected from the group consisting of hydrogen, substituted or unsubstituted alkyl, substituted or unsubstituted cycloalkyl, substituted or unsubstituted aryl, substituted or unsubstituted heteroaryl, and substituted or unsubstituted aralkyl;

each R³ is independently selected from the group consisting of hydrogen, substituted or unsubstituted alkyl, substituted or unsubstituted cycloalkyl, substituted or unsubstituted aryl, substituted or unsubstituted heteroaryl, and substituted or unsubstituted aralkyl;

each R⁴ is independently selected from the group consisting of hydrogen, substituted or unsubstituted alkyl, substituted or unsubstituted cycloalkyl, substituted or unsubstituted aryl, and substituted or unsubstituted aralkyl, and any two R³s may join together to form a cycloalkyl, cycloheteroalkyl ring;

and one of R³s and one of R⁴s on carbon atoms adjacent to X' may join together to form a heterocyclic ring of 5-7 atoms.

11. The composition according to claim 9, wherein L is no atom, R¹ is tert-butyl, R² is hydrogen, and Cy is

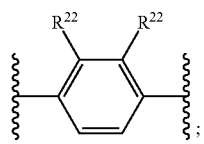

wherein:

each R²² is independently selected from the group consisting of hydrogen, substituted or unsubstituted alkyl, substituted or unsubstituted alkyl, substituted or unsubstituted arylalkyl, substituted or unsubstituted cycloalkyl, substituted or unsubstituted cycloheteroalkyl, substituted or unsubstituted heteroalkyl, substituted or unsubstituted heteroaryl, and substituted or unsubstituted heteroarylalkyl.

12. The composition according to claim 11, wherein each R²² is hydrogen.

13. The composition according to claim 11, wherein R is hydrogen.

14. The composition according to claim 11, wherein each R²² is hydrogen, and R is hydrogen.

15. The composition according to claim 10, wherein said compound is symmetrical.

16. The composition according to claim 10, wherein L is no atom, R¹ is tert-butyl, R² is hydrogen, and Cy is

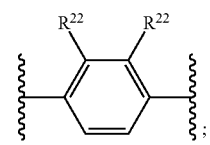

wherein:

each R²² is independently selected from the group consisting of hydrogen, substituted or unsubstituted alkyl, substituted or unsubstituted alkyl, substituted or unsubstituted arylalkyl, substituted or unsubstituted cycloalkyl, substituted or unsubstituted cycloheteroalkyl, substituted or unsubstituted heteroalkyl, substituted or unsubstituted heteroaryl, and substituted or unsubstituted heteroarylalkyl.

17. The composition according to claim 16, wherein each R²² is hydrogen.

18. The composition according to claim 9, wherein said composition is a pharmaceutical preparation.

19. A compound is selected from the group consisting of:

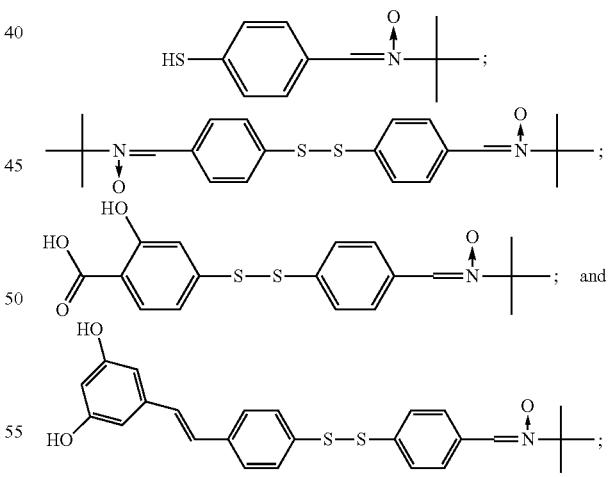

or a pharmaceutically acceptable salt thereof, or a spatial isomer thereof.

* * * * *